United States Patent
Polf et al.

(10) Patent No.: US 10,502,845 B2
(45) Date of Patent: Dec. 10, 2019

(54) TECHNIQUES FOR PRODUCING AN IMAGE OF RADIOACTIVE EMISSIONS USING A COMPTON CAMERA

(71) Applicant: University Of Maryland, Baltimore, Baltimore, MD (US)

(72) Inventors: Jerimy Polf, Towson, MD (US); Emily Draeger, Baltimore, MD (US); Stephen Peterson, Claremont (ZA); Dennis Mackin, Houston, TX (US); A. Sam Beddar, Houston, TX (US)

(73) Assignees: University Of Baltimore, Maryland, Baltimore, MD (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/738,597

(22) PCT Filed: Jun. 24, 2016

(86) PCT No.: PCT/US2016/039256
§ 371 (c)(1),
(2) Date: Dec. 21, 2017

(87) PCT Pub. No.: WO2016/210269
PCT Pub. Date: Dec. 29, 2016

(65) Prior Publication Data
US 2018/0188392 A1 Jul. 5, 2018

Related U.S. Application Data

(60) Provisional application No. 62/191,444, filed on Jul. 12, 2015, provisional application No. 62/184,310, filed on Jun. 25, 2015.

(51) Int. Cl.
*G01T 1/29* (2006.01)
*A61N 5/10* (2006.01)
(Continued)

(52) U.S. Cl.
CPC .............. *G01T 1/29* (2013.01); *A61N 5/1048* (2013.01); *A61N 5/1049* (2013.01); *G01T 1/249* (2013.01);
(Continued)

(58) Field of Classification Search
CPC .... G01T 1/29; G01T 1/24; G01T 1/20; A61N 5/1049; A61N 2005/1054;
(Continued)

(56) References Cited

U.S. PATENT DOCUMENTS 6,269,144 B1  7/2001 Dube et al.
2005/0058242 A1  3/2005 Peschmann
(Continued)

OTHER PUBLICATIONS

ISA/U.S. International Search Report and Written Opinion, International Patent Application No. PCT/US2016/039256, dated Oct. 28, 2016, pp. 1-16.
(Continued)

*Primary Examiner* — David P Porta
*Assistant Examiner* — Fani Boosalis
(74) *Attorney, Agent, or Firm* — Beusse Wolter Sanks & Maire; Eugene J. Molinelli

(57) ABSTRACT

Techniques for imaging radioactive emission in a target volume include collecting from each of multiple detectors in a Compton camera, within a coincidence time interval, location and deposited energy from an interaction associated with each high energy particle source event in a target volume, for N source events. A cone of possible locations for each source event is determined based on the locations and deposited energies collected. A SOE algorithm is initiated by selecting a random location on the cone and generating a histogram that indicates, a count of the selected locations that occur inside each voxel of the target volume. N solution locations for the N source events are determined after L (Continued)

iterations by updating the selected location on a corresponding cone based at least in part on values of the counts in the histogram excluding the current source event. A solution is presented on a display device.

12 Claims, 12 Drawing Sheets

(51) Int. Cl.
  *G01T 1/24*       (2006.01)
  *G01T 1/164*      (2006.01)
  *G01T 1/20*       (2006.01)
  *G06T 11/20*      (2006.01)

(52) U.S. Cl.
  CPC .............. *A61N 2005/1052* (2013.01); *A61N 2005/1054* (2013.01); *A61N 2005/1087* (2013.01); *G01T 1/1642* (2013.01); *G01T 1/20* (2013.01); *G01T 1/24* (2013.01); *G06T 11/206* (2013.01); *G06T 2210/41* (2013.01)

(58) Field of Classification Search
  CPC .......... A61N 2005/1087; A61N 5/1048; G06T 11/206; G06T 2210/41
  See application file for complete search history.

(56) References Cited

U.S. PATENT DOCUMENTS

| | | | |
|---|---|---|---|
| 2010/0301221 A1 | 12/2010 | Nakamura | |
| 2011/0218432 A1* | 9/2011 | Tumer | A61B 6/00 600/431 |
| 2011/0260071 A1 | 10/2011 | Yamaguchi et al. | |
| 2014/0072200 A1 | 3/2014 | Yamaguchi | |

OTHER PUBLICATIONS

Mackin et al., "Evaluation of a stochastic reconstruction algorithm for use in Compton camera imaging and beam range verification from secondary gamma emission during proton therapy," Phys Med Biolo., Jun. 7, 2012, pp. 1-21.

Agostinelli, S., et al., "Geant4—a simulation toolkit," Nuclear Instruments & Methods in Physics Research, 2003, pp. 250-303, vol. A, No. 506, doi:10.1016/S0168-9002(03)01368-8, Publisher: Elsevier.

Andreyev, A., et al., "Fast image reconstruction for Compton camera using stochastic origin ensemble approach," The International Journal of Medical Physics Research and Practice, 2010, pp. 429-438, vol. 38, No. 1, doi.10.1118/1.3528170, Publisher: Medical Physics.

Bennett, G.W., et al., "Visualization and Transport of Positron Emission from Proton Activation in vivo," Science, New Series, 1978, pp. 1151-1153, vol. 200, No. 4346, Publisher: American Association for the Advancement of Science.

Brun, R., et al., "ROOT—An object oriented data analysis framework," Nuclear Instruments and Methods in Physics Research, Section A, 1997, pp. 81-86, vol. 389, No. 1-2, doi.10.1016/S0168-9002(97)00048-X, Publisher: Elsevier.

Deleplanque, M.A., et al., "GRETA: utilizing new concepts in y-ray detection," Nuclear Instruments & Methods in Physics Research, Section A, 1999, pp. 292-310, vol. 430, Publisher: Elsevier.

Enghardt, W., et al., "In-beam PET at high-energy photon beams: a feasibility study," Physics in Medicine and Biology, 2006, pp. 1779-1789, vol. 51, No. 7, doi.10.1088/0031-9155/51/7/010, Publisher: IOP Publishing.

Herbert, T., et al., "Three-dimensional maximum-likelihood reconstruction for an electronically collimated single-photon-emission imaging system," Journal of the Optical Society of America, 1990, pp. 1305-1313, vol. 7, No. 7, doi.10.1364/JOSAA.7.001305, Publisher: OSA Publishing.

Kang, B.H., et al., "Monte Carlo Design Study of a Gamma Detector System to Locate Distal Dose Falloff in Proton Therapy," IEEE Transactions on Nuclear Science, 2009, pp. 46-50, vol. 56, No. 1, doi.10.1109/TNS.2008.2005189, Publisher: IEEE.

Kim, S.M., et al., "Two approaches to implementing projector-backprojector pairs for 3D reconstruction from Compton scattered data," Nuclear Instruments and Methods in Physics Research, Section A, 2006, pp. 255-258, vol. 571, No. 1-2, doi:10.1016/j.nima.2006.10.076, Publisher: Elsevier.

Knopf, A., et al., "Quantitative assessment of the physical potential of proton beam range verification with PET/CT," Physics in Medicine and Biology, 2008, pp. 4137-4151, vol. 53, No. 15, doi.10.1088/0031-9155/53/15/009, Publisher: IOP Publishing.

Kroeger, R. A., et al., "Three-Compton Telescope: Theory, Simulations, and Performance," IEEE Transactions on Nuclear Science, 2002, pp. 1887-1892, vol. 49, No. 4, doi:10.1109/TNS.2002.801539, Publisher: IEEE.

Kurfess, J.D., et al., "Considerations for the Next Compton Telescope Mission," AIP Conference Proceedings, 5th Compton Symposium, 2000, pp. 789-793, vol. 510, DOI: 101063/1.1303306, Publisher: AIP Publishing LLC.

L'Ecuyer, P., et al., "Maximally Equidistributed Combined Tausworthe Generators," Mathematics of Computation, 1996, pp. 203-213, vol. 65, No. 213, Publisher: American Mathematical Society.

Litzenberg, D.W., et al., "On-line Monitoring and P.E.T. Imaging of Proton Radiotherapy Beams," Nuclear Science Symposium and Medical Imaging Conference, 1992, Conference Record of the 1992 IEEE, vol. 4, doi:10.1109/NSSMIC.1992.301095, Publisher: IEEE XPlore.

Mackin, D., et al., "Evaluation of a stochastic reconstruction algorithm for use in Compton camera imaging and beam range verification from secondary gamma emission during proton therapy," Physics in Medicine and Biology, 2012, pp. 3537-3553, vol. 57, No. 11, doi: 10.1088/0031-9155/57/11/3537, Publisher: IOP Publishing.

Mackin, D., et al., "The effects of Doppler broadening and detector resolution on the performance of three-stage Compton cameras," The International Journal of Medical Physics Research and Practice, 2012, pp. 0124021-12, vol. 40, No. 1, doi.org/10.1118/1.4767756, Publisher: Medical Physics.

McCleskey, M., et al., "Evaluation of a multistage CdZnTe Compton camera for prompt γ imaging for proton therapy," Nuclear Instruments and Methods in Physics Research A, 2015, pp. 163-169, vol. 785, doi.org/10.1016/j.nima.2015.02.030, Publisher: Elsevier.

Min, C.H., et al., "Prompt gamma measurements for locating the dose falloff region in the proton therapy," Applied Physics Letters, 2006, pp. 1835171-3, vol. 89, No. 18, doi:10.1063/1.2378561, Publisher: AIP Publishing LLC.

Moteabbed, M., et al., "Monte Carlo patient study on the comparison of prompt gamma and PET imaging for range verification in proton therapy," Physics in Medicine and Biology, 2011, pp. 1063-1082, vol. 56, No. 4, doi: 10.1088/0031-9155/56/4/012, Publisher: IOP Publishing.

Mundy, D.W., et al., "Uncertainty analysis of a Compton camera imaging system for radiation therapy dose reconstruction," The International Journal of Medical Physics Research and Practice, 2010, pp. 2341-2350, vol. 37, No. 5, doi: 10.1118/1.3399777, Publisher: Medical Physics.

Paans, A., et al., "Proton therapy in combination with pet as monitor: a feasibility study," IEEE Transactions on Nuclear Science, 1993, pp. 1041-1044, vol. 40, No. 4, doi: 10.1109/23.256709, Publisher: IEEE.

Parodi, K., et al., "Potential application of PET in quality assurance of proton therapy," Physics in Medicine and Biology, 2000, pp. N151-N156, vol. 45, No. 11, doi: 10.1088/0031-9155/45/11/403, Publisher: IOP Science.

Parzen, E., "On estimation of a probability density function and mode," The Annals of Mathematical Statistics, 1962, pp. 1065-1076, vol. 33, No. 3, doi:10.1214/aoms/1177704472, Publisher: Institute of Mathematical Statistics.

(56) References Cited

OTHER PUBLICATIONS

Peterson, S., et al., "Optimizing a three-stage Compton camera for measuring prompt gamma rays emitted during proton radiotherapy," Physics in Medicine and Biology, 2010, pp. 6841-6856, vol. 55, No. 22, doi:10.1088/0031-9155/55/22/015, Publisher: IOP Publishing.

Phillips, G.W., "Gamma-ray imaging with Compton cameras," Nuclear Instruments and Methods in Physics Research B, 1995, pp. 674-677, vol. 99, No. 1, doi: 10.1016/0168-583X(95)80085-9, Publisher: Elsevier.

Polf, J.C., et al., "Measurement and calculation of characteristic prompt gamma ray spectra emitted during proton irradiation," Physics in Medicine and Biology, 2009, pp. N519-N527, vol. 54, No. 22, doi:10.1088/0031-9155/54/22/N02, Publisher: IOP Publishing.

Polf, J.C., et al., "Prompt gamma-ray emission from biological tissues during proton irradiation: a preliminary study," Physics in Medicine and Biology, 2009, pp. 731-743, vol. 54, No. 3, doi: 10.1088/0031-9155/54/3/017, Publisher: IOP Publishing.

Robertson, D., et al., "Material efficiency studies for a Compton camera designed to measure characteristic prompt gamma rays emitted during proton beam radiotherapy," Physics in Medicine and Biology, 2011, pp. 3047-3059, vol. 56, No. 10, doi: 10.1088/0031-9155/56/10/010, Publisher: IOP Publishing.

Rosenblatt, M., "Remarks on some nonparametric estimates of a density function," The Annals of Mathematical Statistics, 1956, pp. 832-837, vol. 27, No. 3, doi: 10.1214/aoms/1177728190, Publisher: Institute of Mathematical Statistics.

Schmid, G., et al., "A y-ray tracking algorithm for the GRETA spectrometer," Nuclear Instruments and Methods in Physics Research A, 1999, pp. 69-83, vol. 430, No. 1, doi: 10.1016/S0168-9002(99)00188-6, Publisher: Elsevier.

Siddon, R.L., "Fast calculation of the exact radiological path for a three-dimensional CT array," Physics in Medicine and Biology, 1985, pp. 252-255, vol. 12, No. 2, doi: 10.1118/1.595715, Publisher: IOP Publishing.

Sitek, A., "Representation of photon limited data in emission tomography using origin ensembles," Physics in Medicine and Biology, 2008, pp. 3201-3216, vol. 53, No. 12, doi: 10.1088/0031-9155/53/12/009, Publisher: IOP Publishing.

Solomon, C.J., et al., "Gamma ray imaging with silicon detectors—a compton camera for radionuclide imaging in medicine," Nuclear Instruments and Methods in Physics Research A273, 1988, pp. 787-792, vol. 273, No. 2-3, doi: 10.1016/0168-9002(88)90097-6, Publisher: Elsevier.

Testa, E., et al., "Dose profile monitoring with carbon ions by means of prompt-gamma measurements," Nuclear Instruments and Methods in Physics Research B, 2009, pp. 993-996, vol. 267, doi: 10.1016/j.nimb.2009.02.031, Publisher: Elsevier.

Wilderman, S.J., et al., "Fast Algorithm for List Mode Back-Projection of Compton Scatter Camera Data," IEEE Transactions on Nuclear Science, 1998, pp. 957-962, vol. 45, No. 3, doi: 10.1109/NSSMIC.1997.672609, Publisher: IEEE.

Zhang, F., et al., "New Readout Electronics for 3-D Position Sensitive CdZnTe/HgI2 Detector Arrays," IEEE Transactions on Nuclear Science, 2006, pp. 3021-3027, vol. 53, No. 5, doi: 10.1109/TNS.2007.902354, Publisher: IEEE.

\* cited by examiner

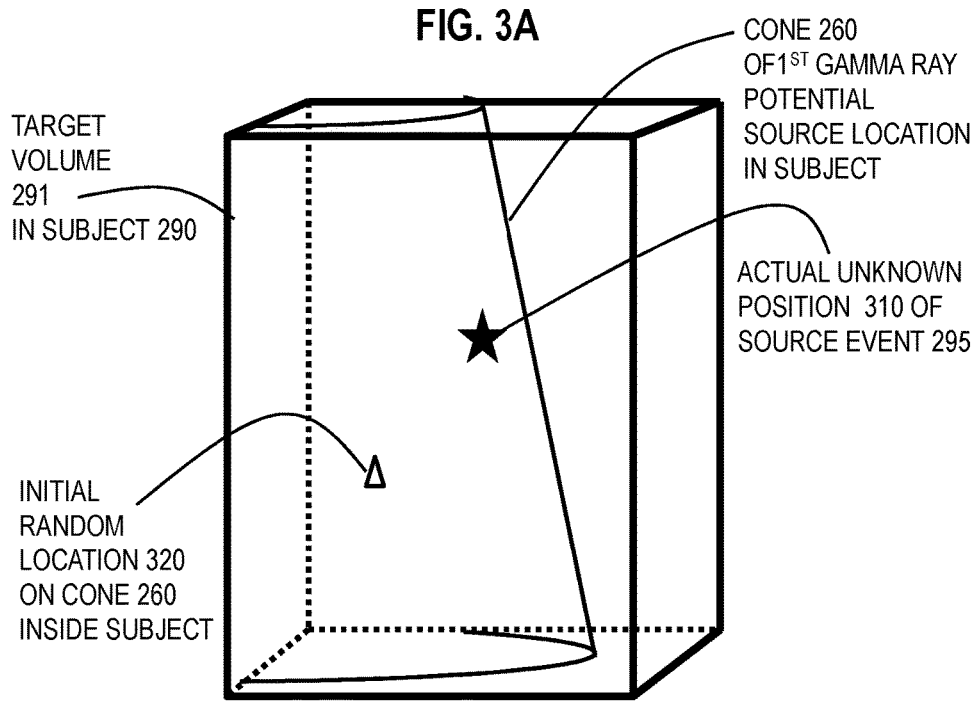
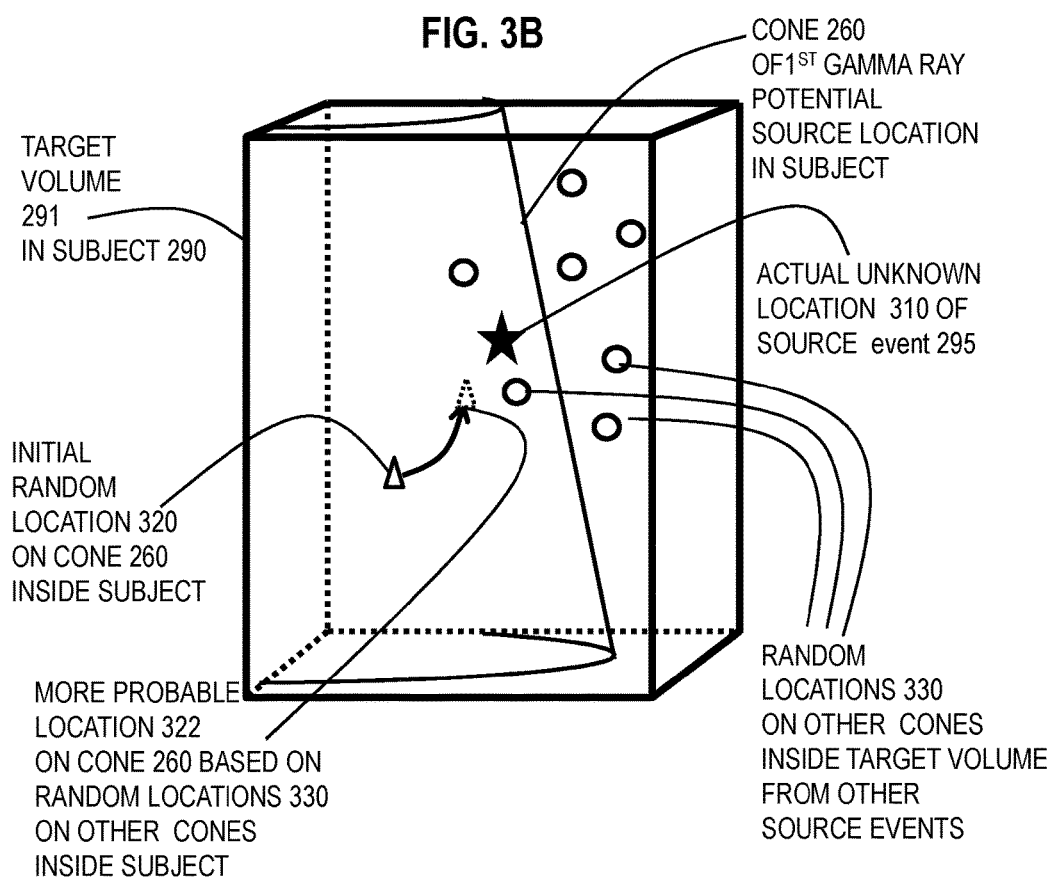

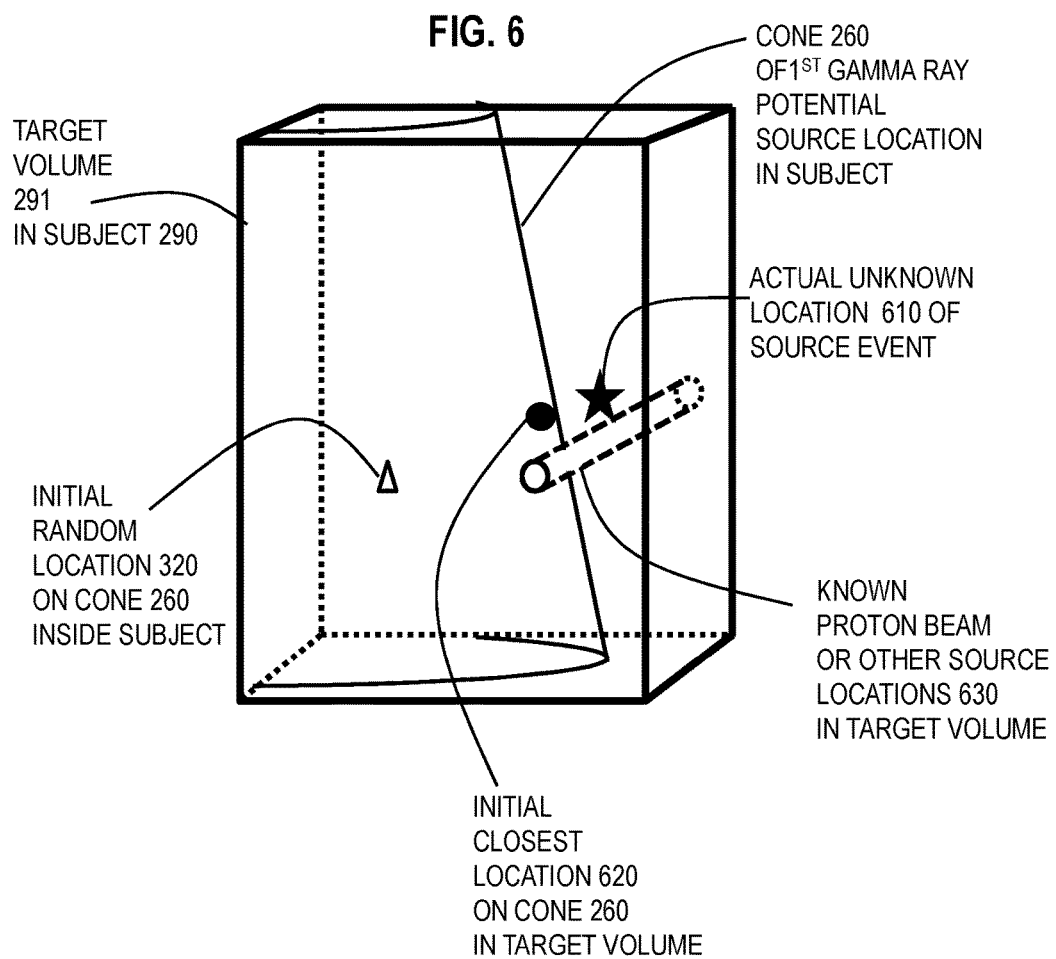

TECHNIQUES FOR PRODUCING AN IMAGE OF RADIOACTIVE EMISSIONS USING A COMPTON CAMERA

CROSS-REFERENCE TO RELATED APPLICATIONS

This application is a 371 national stage application of PCT Application No. PCT/US2016/039256 filed Jun. 24, 2016 which claims benefit of Provisional Appln. 62/184,310, filed Jun. 25, 2015, and claims benefit of Provisional Appln. 62/191,444, filed Jul. 12, 2015 the entire contents of each of which are hereby incorporated by reference as if fully set forth herein, under 35 U.S.C. § 119(e).

BACKGROUND

The use of proton therapy for treating cancer has greatly increased over the past decade, mostly because of the advantageous interaction properties of proton beams. A proton beam initially deposits a relatively low dose upon entering the patient, and the deposited dose rises to a sharp maximum, known as the Bragg peak, near the end of the beam's range in the patient. The sharp Bragg peak and the finite range of the beam provide the ability to deliver a highly conformal treatment, allowing for dose escalation to the tumor and/or a reduction of exposure to the surrounding healthy tissues. However, errors in patient setup or positioning, day-to-day variations in internal anatomy, anatomical motion, changes to tumor and normal tissue in response to treatment, and other biological factors all lead to uncertainties in the exact position of the distal dose gradient within the patient. Because of uncertainties in the position of the distal falloff, standard proton treatment techniques include the use of large treatment volume expansions to ensure target coverage and to avoid any possible undershoot or overshoot of the beam into nearby critical structures. These large safety margins limit the ability to exploit the steep dose gradients at the distal edge of the Bragg peak, thus reducing the full clinical potential of proton radiation therapy. Therefore, there has been a recognized need for a method of verifying the in vivo beam range, to allow for a reduction in necessary treatment margins and to improve our ability to fully exploit the advantages of proton radiation therapy.

One method for in vivo range verification consists in measuring secondary gamma radiation emitted from the treated tissue (Bennett et al 1978, Paans et al. 1993, Min et al. 2006). During proton therapy, proton-nucleus interactions produce secondary gamma rays through two distinct methods: (1) by creating positron-emitting isotopes (11C, 15O, etc.) that produce coincident, 511 keV annihilation gammas (positron annihilation; PA), and (2) by leaving behind an intact, excited nucleus that quickly decays by emitting a characteristic prompt (CP) gamma ray, also called PG emissions. Because the excited nuclear states are quantized, excited elemental nuclei emit a characteristic CP gamma spectrum.

Many researchers are currently studying the use of PA (Litzenberg et al 1992, Parodi et al 2000, Enghardt et al 2005, Knopf et al 2008) and CP (Min et al 2006, Polf et al 2009a, Testa et al 2009) gamma emission as a method for in vivo dose range verification. In particular, studies of CP emission during proton therapy have shown that it is strongly correlated to the dose deposited in the patient (Min et al 2006, Polf et al 2009a, Polf et al 2009b, Moteabbed et al 2011) and to the composition and density of the irradiated tissues (Polf et al 2009a, Polf et al 2009b). These studies have focused on techniques for measuring the initial energy spectrum and spatial distribution of CP gammas emitted from tissues. However, because of the relatively high energies (2 MeV-15 MeV) of CP emission from tissue, the efficiency of standard gamma detectors and imagers is very low, and standard collimation techniques are ineffective for CP measurements.

These problems with the standard detectors have led several researchers to study the use of Compton camera imaging (CCI) to measure CP emission during proton irradiation. Compton cameras (CCs) are multiple detector devices (typically with one or more stages) that measure the energy deposition and position for each interaction of a gamma as it scatters in the different detectors of the camera. Because two-stage CCs have low efficiency for gammas with energy greater than about 1 MeV, Kurfess et al (2000) suggested the use of three-stage CCs that do not require the gammas to be completely absorbed. Recent work by Peterson et al (2010) and Robertson et al (2011) has shown that a three-stage CC could provide adequate detection efficiency to allow for measurement and imaging of secondary gammas (both CP and PA) from tissue during proton therapy.

A variety of approaches for reconstructing images from CC data have been studied. ML-EM (maximum-likelihood expectation-maximization) methods were introduced for CT imaging (Siddon 1985) and adapted for use with CC (Hebert et al 1990). A leading list-mode back-projection algorithm was introduced by Wilderman et al. and then improved by Mundy et al. (1998, 2010). Kim et al. compared two iterative forward-projection/back-projection algorithms and showed that these algorithms have better resolution than back-projection alone (2007). More recently, Nguyen et al. showed that the COSEM (complete data ordered subsets expectation maximization) algorithm produces qualitatively better image results when optimized using MAP (maximum a posteriori) than maximum-likelihood. The stochastic origin ensembles (SOE) algorithm, based on the Metropolis-Hastings algorithm, was originally introduced by Sitek (2008) for use in emission tomography. Andreyev et al. (2011) adapted the SOE algorithm to CCI and reconstructed list-mode data from simulated gamma sources embedded in phantoms. They compared their SOE results with the results obtained using the maximum-likelihood expectation-maximization (ML-EM) algorithm (Siddon 1985), designed for CT imaging, and found that SOE was much faster and produced images of similar resolution (Andreyev et al 2011).

SUMMARY

Applicant had determined that it was possible to measure prompt gamma (PG) interactions with a prototype Compton camera during delivery of proton pencil beams at clinical dose rates into a water phantom. Images of the PG emission could be reconstructed and shifts in the Bragg Peak range were detectable. Therefore PG imaging with a Compton camera for in vivo range verification during proton treatment delivery was determined to be feasible. However, improvements in the prototype Compton camera detection efficiency and SOE reconstruction algorithms were desired to make the techniques into a clinically viable PG imaging system. Thus, techniques are provided here for improving the production of an image of radioactive emissions using a Compton camera over approaches previously used. The improvements provide either faster convergence of the reconstruction algorithms, or more accurate results, or are applicable to other types of medical imaging than previously used with Compton cameras.

In a first set of embodiments, a method includes receiving data indicating a set of one or more known positions in a target volume of a subject, which positions are associated with a cause of a high energy particle source event. The method includes collecting from each of multiple detectors in one or more stages of a Compton camera, within a coincidence time interval, location and deposited energy from an interaction associated with a single source event in the target volume of the subject. The method further includes determining, for the source event, a cone of possible locations for the source event based on the locations and deposited energies collected from the detectors of the Compton camera. Still further, the method includes selecting a particular location on the cone within the target volume based on proximity to the set of one or more known positions in the target volume. Yet further, the method includes presenting, on a display device, data indicating the particular location in the target volume.

In a second set of embodiments, a method includes receiving first data indicating locations of a plurality of voxels of target resolution v in a target volume of a subject and collecting from each of multiple detectors in one or more stages of a Compton camera, within a coincidence time interval, location and deposited energy from an interaction associated with each high energy particle source event in the target volume, for N source events in the target volume. The method includes determining, for each source event, a cone of possible locations for the source event based on the locations and deposited energies collected from the detectors of the Compton camera. The method also includes initiating a stochastic origins ensemble (SOE) method, which is an iterative algorithm, by selecting for each source event a random location on the cone of possible locations for a corresponding source event and generating a histogram that indicates, for each voxel, a count of the selected locations that occur inside the voxel. Still further, the method includes determining a solution made up of a set of N solution locations for the N source events from the SOE iterative algorithm after L iterations by updating for each source event during each iteration the selected location on the corresponding cone based at least in part on values of the counts in the histogram excluding the current source event, and updating the histogram based on the updated selected location for each source event during each iteration. Still further, the method includes presenting, on a display device, data that indicates at least one solution location of the set of N solution locations.

In a third set of embodiments, a method includes: step a for receiving first data indicating locations of a plurality of voxels of target resolution v in a volume of a subject; and, step b for collecting from each of a plurality of detectors in one or more stages of a Compton camera within a coincidence time interval, location and deposited energy from an interaction associated with each high energy particle source event in the subject volume, for a plurality of N source events in the subject volume. The method also includes step c for determining, for each source event, a cone of possible locations for the source event based on the locations and deposited energies collected from the plurality of detectors in one or more stages of the Compton camera. The method still further includes step d for initiating an instance of a stochastic origins ensemble (SOE) iterative algorithm by selecting for each source event a random location on the cone of possible locations for a corresponding source event.

Yet further, the method includes step e for determining an instance of a solution made up of a set of N solution locations for the N source events from the SOE iterative algorithm after L iterations. Even further, the method includes step f for repeating steps d and e for a plurality of M instances of the SOE iterative algorithm by selecting for each source event M different random locations on the cone to initiate the plurality of M instances and to determine a plurality of M instances of a solution. The method still further includes step g for combining the plurality of M instances of the solution location for each source event to determine a combined solution location for each of the N source events. The method also yet further includes step h for presenting, on a display device, data indicating the combined solution location for at least one source event of the N source events.

In each set of embodiments, in some embodiments the source event is a gamma ray emission and the cause of the source event is a proton beam interacting with an atom in the subject.

In each set of embodiments, in some embodiments the source event is a gamma ray emission and the cause of the source event is a positron-emitting radionuclide as used in positron emission tomography (PET) medical imaging. In some of these embodiments, collecting location and deposited energy from the interaction associated with the source event also includes selecting from each of only two detectors in one or more stages of the Compton camera within the coincidence time interval, location and deposited energy such that a sum of the deposited energies in the two detectors is about equal to an energy of a gamma ray emitted by annihilation of the positron produced by the positron-emitting radionuclide.

In each set of embodiments, in some embodiments the source event is a gamma ray emission and the cause of the source event is a gamma-emitting radioisotope as used in single-photon emission computed tomography (SPECT) medical imaging. In some of these embodiments, collecting location and deposited energy from the interaction associated with the source event also includes selecting from each of only two detectors in one or more stages of the Compton camera within the coincidence time interval, location and deposited energy such that a sum of the deposited energies in the two detectors is about equal to an energy of a gamma ray emitted by the gamma-emitting radioisotope.

In other sets of embodiments, a computer-readable medium or system is configured to perform one or more steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 3A is a block diagram that illustrates an example intersection of cone of possible source positions within a target volume, according to an embodiment;

FIG. 3B is a block diagram that illustrates an example iteration of stochastic origin ensemble (SOE) method for positioning events from spatially related sources, according to an embodiment;

FIG. 6 is a block diagram that illustrates an example closest location to a known gamma source on a cone of possible source positions, according to an embodiment;

DETAILED DESCRIPTION

Figure 1:
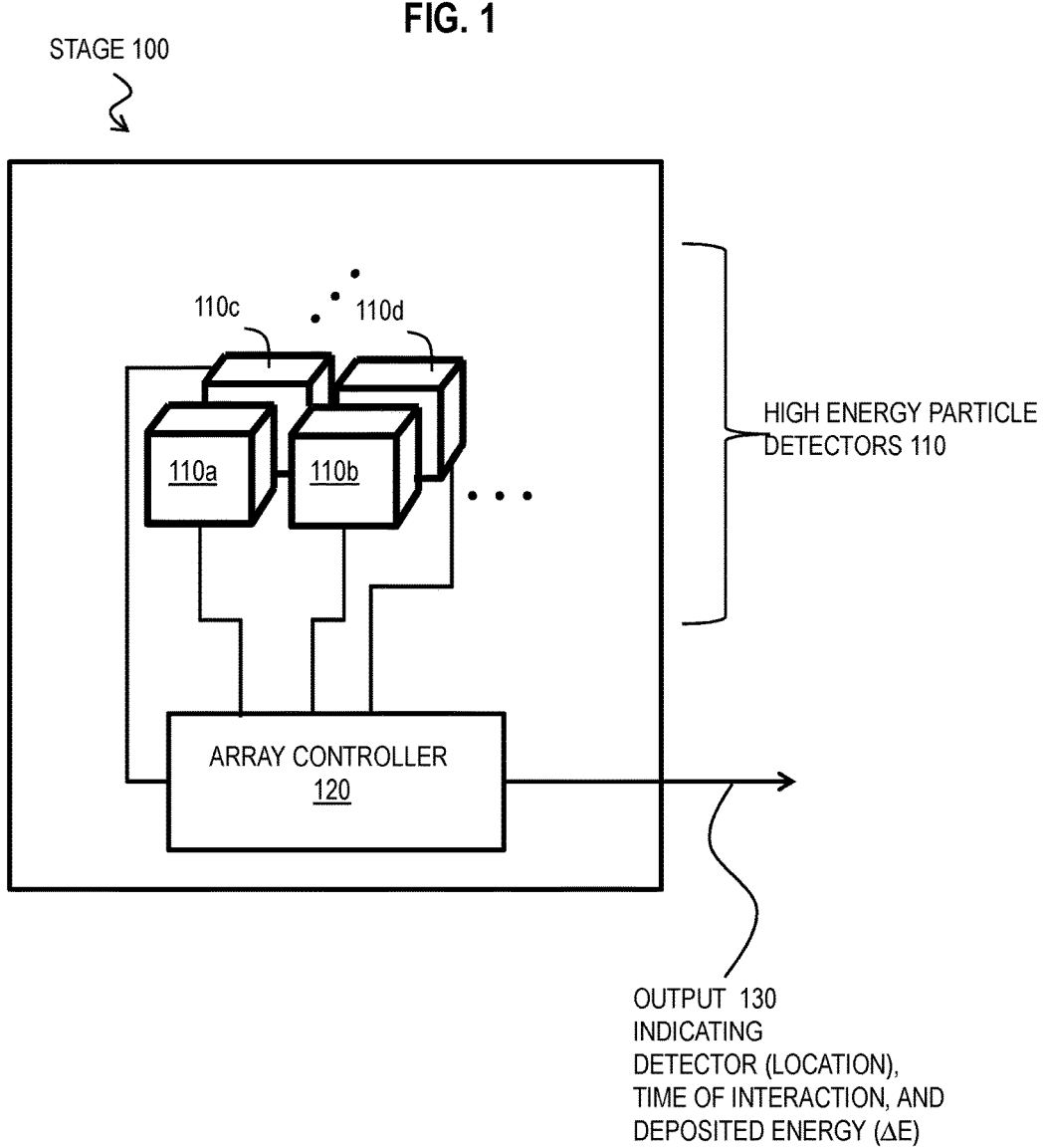
FIG. 1 is a block diagram that illustrates an example array of high energy particle detectors comprising one stage of a Compton camera, according to an embodiment.

A method and apparatus are described for production of an image of radioactive emissions using a Compton camera. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of detecting gamma rays (photons) emitted from inside a living subject (e.g., a human or animal) during various medical applications. However, the invention is not limited to this context. In other embodiments, other high energy particles, including alpha rays (helium nuclei), beta rays (electrons), beta plus rays (positrons), and X-rays (photons), are detected using Compton scattering in a suitable designed Compton camera due to other sources of such radiation in living and non-living subjects (such as machines, buildings and geological formations).

1. OVERVIEW

Compton interactions, also referred to as Compton scattering, occur when a photon or other high energy particle of wavelength lambda strikes an electron at rest in a material (including a living tissue). After the collision, a photon or other high energy particle is scattered at an angle $\theta$ with decreased energy and corresponding increased wavelength $\lambda'$. The increased wavelength is due to the particle's lower energy (and lower frequency, f) from the collision, according to the equations $\lambda=c/f$ and $E=h*f$, where h is Planck's constant. The electron moves away with a speed s in a direction $\phi$. Thus, at each Compton scattering interaction the high energy particle loses a part of its energy to a recoiling electron within the material or tissue. The scattering parameters satisfy the laws of conservation of energy and momentum. The Compton scattering relationship is given by Equation 1.

$$\Delta\lambda = \frac{h}{m_0 c}(1 - \cos\theta) \qquad (1)$$

The interaction is detected in a stage of a Compton camera, as described below. Each stage provides a measurement of an amount of energy deposited in a detector and a location within the detector within a time window called a coincidence time interval. As used herein, the term interaction when used for one particle impinging on a different target particle includes either scattering of a particle of lower energy than the impinging particle or absorption of the impinging particle as energy is transferred to a component of a target particle. Typically each stage of a Compton camera has a one-dimensional (1D), or two dimensional (2D) or three dimensional (3D) array of detectors. Angles are determined by detecting successive scattering (e.g., a subsequent Compton scattering by the emitted lower energy particle) in a second, different detector of a Compton camera. As used herein, a high energy particle emission source event (simply called a source event or emission event hereinafter) refers to a single high energy particle emission within a subject that leads to a succession of two or more interactions, including at least one Compton scattering interaction, detected in corresponding detectors or stages of a Compton camera.

Various embodiments use the interactions in two or more detectors of a Compton camera to infer the position, or position and energy, of the source event in a target volume of a subject, such as gamma ray photon source events, x-ray photon source events, high energy electron or positron source events, among others. The energy of the initial high energy particle can be estimated by summing the energies deposited in all the detectors of the Compton camera, if enough detectors are included.

In the illustrated embodiments, for medical imaging of proton beams, PET, and SPECT, a Compton camera consists of one or more stages, with each stage including an array of high energy (1 to 100 million electron volts, MeV) photon detectors that span across the frequencies of high energy X-rays and gamma rays. In other embodiments, other detectors are used. The cameras are suitable for measuring Compton interactions, in which the energy deposited in a detector is related to the scattering angle between impinging and scattered photons or other high speed particles. If the emitted angle is detected based on a subsequent interaction in a second detector or stage, then the initial angle can be determined from the emitted angle and the energy deposited in the first stage, according to the equations given below. That angle defines a cone of possible positions for the source event. The probable location of the source event is on the cone and within the subject.

The energy deposited at each stage and the wavelength after each scattering are governed by the following equations applicable to X-ray photons, high energy electrons (beta rays) positrons (beta plus rays) and helium nuclei (alpha rays) among others. The recorded detector interaction positions and energy depositions in the CC are used to calculate the initial energy of the ray ($E_0$) using the formula (Kroeger et al 2002) given by Equation 2A.

$$E_0 = \Delta E_1 + \frac{1}{2}\left(\Delta E_2 + \sqrt{\Delta E_2^2 + \frac{4\Delta E_2 m_e c^2}{1 - \cos\theta_2}}\right), \quad (2A)$$

where $\Delta E_1$ and $\Delta E_2$ are the energies deposited by the first and second scatters, $\theta_2$ is the second scattering angle between the first interaction in one detector and the next interaction in another detector or stage, $m_e$ is the mass of the electron, and c is the speed of light. In some gamma ray embodiments, there is no third interaction and the scattered photon is photo-absorbed in the second detector or stage. In this case, the computation of $E_0$ is simpler, given by Equation 2B.

$$E_0 = \Delta E_1 + \Delta E_2 \quad (2B)$$

After $E_0$ has been calculated, the initial scattering angle $\theta_1$ is calculated using the Compton scattering formula:

$$\cos\theta_1 = 1 + m_e c^2 \left(\frac{1}{E_0} - \frac{1}{E_0 - \Delta E_1}\right). \quad (3)$$

In various embodiments, the cameras are designed to resolve the angles of sources emitting high energy particles, where the sources are distributed over volumes of tens to hundreds of cubic millimeters within a target volume of hundreds of cubic centimeters inside a subject. As described in more detail in another section, the characteristics of such source events and/or their precise locations are of clinical significance in proton beam therapy, positron emission tomography (PET) medical imaging, and single-photon emission computed tomography (SPECT) medial imaging, among others. To be useful clinically, the reconstruction algorithm must be both fast (taking a few hours or less) and precise, with resolution on the order of about 1 millimeter (mm, 1 mm=10-3 meters).

As noted in the background section, such radiographic imaging or therapy techniques causes the emission of prompt gamma rays resulting from the interactions of an incident beam (a proton beam for example) with a source tissue (during proton beam radiation therapy, for example). The emissions are prompt because they occur without appreciable delay. The interactions in multiple detectors in one or more stages of the Compton camera from a single source event necessarily occurs within a short time window, on the order of several nanoseconds (ns, 1 ns=$10^{-9}$ seconds) as the particles travel at or close to the speed of light (about $3 \times 10^8$ meters per second) over the several centimeter (cm, 1 cm=$10^{-2}$ meters) distances between the stages. In practical terms, interactions in multiple detectors in one or more stages are assumed to be due to the same source event if the interactions all occur in a coincidence time interval short compared to the average time between source events. The detector interactions can occur in the stages in any order. For instance, stage 1 then 2 then 3, or stage 3 then 1 then 2, or stage 2 then 1 then 3, etc. All are valid interactions associated with a single emission event as long the correct sequence is determined. In example embodiments, for proton beams as the source of gamma rays detected in a Compton camera, the coincidence time interval is about 10 microseconds (μs, 1 μs=$10^{-6}$ seconds).

Compton cameras are high energy particle emission event detectors including one or more detection stages that each measure the energy deposition, the time, and the position of each interaction as successive rays due to a single source event scatter or absorb in each detector of the camera. In a Compton camera, images of source event locations are created by determining for each of multiple source events (in multiple separate coincidence time intervals) the energy deposited and the spatial coordinates of interactions within multiple detectors within the Compton camera. An example single stage is illustrated in FIG. 1 and an example three stage camera is illustrated in FIG. 2.

FIG. 1 is a block diagram that illustrates an example stage 100 of a Compton camera, comprising a 2D array 110 of high energy particle detectors 110*a*, 110*b*, 110*c* and 110*d* plus additional detectors indicated by ellipses. In some embodiments, each detector has an extended size in one or more directions yet can detect a location within a resolution size smaller than the volume of the detector. An array controller 120 receives input signals from the detectors 110*a*, 110*b*, 110*c*, and 110*d*, processes the signals and generates an output signal 130 indicating the detector (or associated location of the detector or within the detector), time of interaction, and amount of energy deposited (ΔE). If semiconductor crystals are used, then the detectors in each stage are usually composed arrays of small crystals capable of resolving the target resolution (such as crystals of about 2 cm×2 cm×1 cm for proton beam applications) with all crystals in the array electronically connected so they act as a single large area detector. If a camera uses scintillating crystals, then each stage can have a single scintillator (such as about 10 cm×10 cm×5 cm for the proton beam applications) or could have an array of small scintillating rods (such as about 1 cm×1 cm×5 cm for proton beam applications) sandwiched together to form a large crystal. The more detectors the more particles are detected and thus the higher efficiency for the intended use, such as enough detectors to properly evaluate the proton beam Bragg Peak with 20% of the dose delivered for the proton beam therapy applications).

Figure 2:
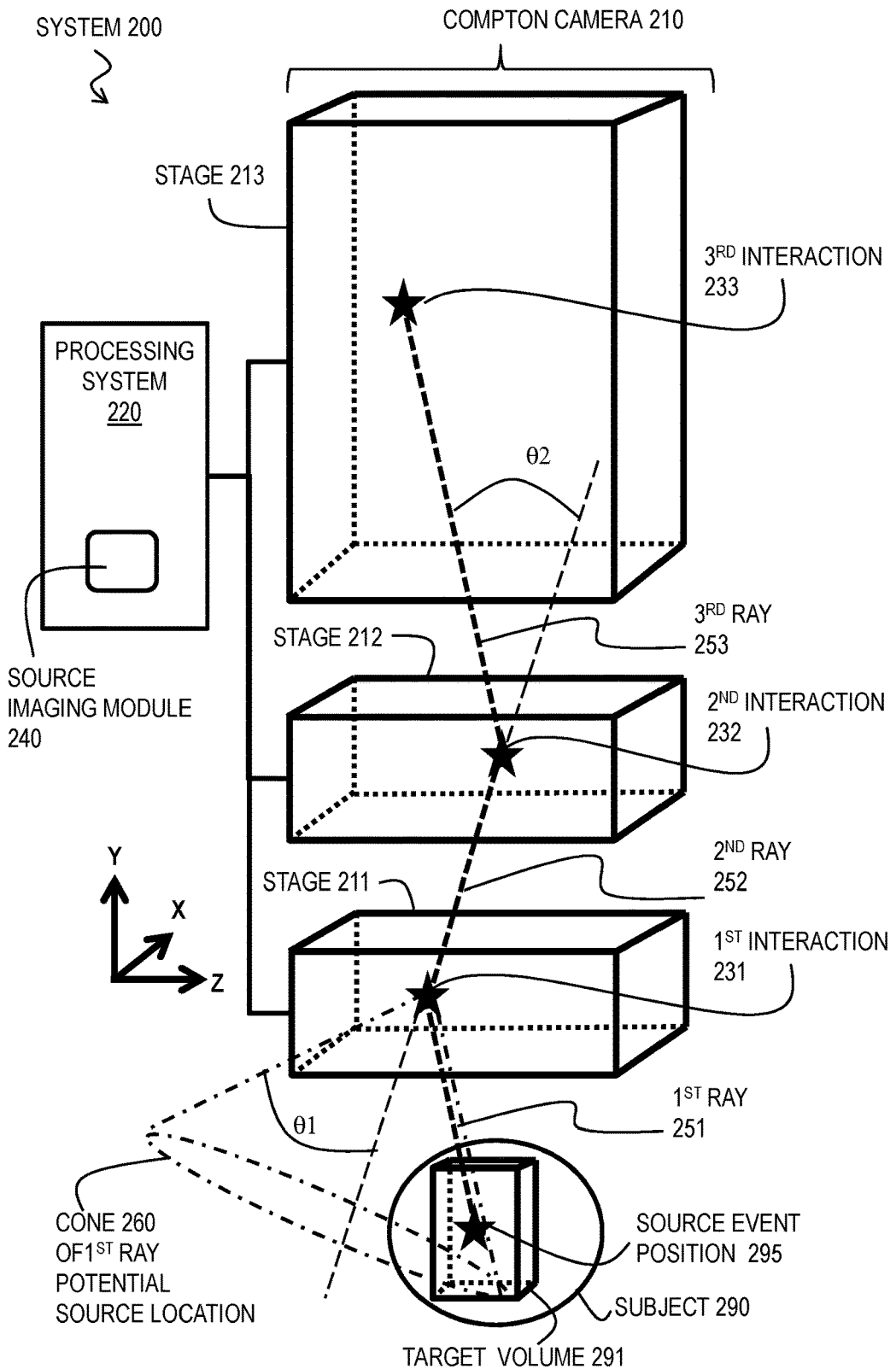
FIG. 2 is a block diagram that illustrates an example Compton camera system suitable for imaging source events in a subject volume, according to an embodiment.

FIG. 2 is a block diagram that illustrates an example Compton camera system 200 suitable for imaging source events in a subject volume, according to an embodiment. Although a subject 290 is depicted for purposes of illustration, the subject is not part of the system 200. FIG. 2 depicts a three-stage interaction or triple scatter Compton camera 210, comprising stages 211, 212 and 213. The spatial coordinate system of the system 200 is given by the x and z axes in the horizontal plane of the diagram and the y axis in the vertical direction. In some embodiments, the origin of the spatial coordinates is related to the target volume, e.g., at the center or edge of the target volume. Although the stages 211, 212 and 213 are separated vertically in FIG. 2, there is no requirement that the orientation of the system be aligned with the local vertical or the gravitational field. Depending on the energies and interaction rates expected, one stage can be beside another instead of displaced in the same direction as two previous stages, as depicted in FIG. 2. The output from the stages are input to a processing system, such as local or remote computer systems depicted in FIG. 11 or chip set depicted in FIG. 112. The processor is configured with software or hardware or both that function as a source imaging module 240 that performs one or more steps of an imaging method described in more detail below with reference to FIG. 7.

The operation of the Compton camera is illustrated by a single source event that initiates a succession of rays that interact with different stages of the Compton camera 210. The position of the single source event occurs at position 295 in subject 290, due to any one of various causes, such as a proton beam interacting with material in subject 290 or radioactive decay from a naturally occurring or implanted radiation source, or some combination. In some embodiments, some information is known about the cause of the source event, such as the location of the implanted radioactive source, or the axis of the proton beam or the energy, or some combination; and, such information is used to simplify the design of the camera or simplify computations to produce the image. However, in some embodiments, the source events can be imaged even in the absence of such information.

The result is the emission of a first ray 251 of unknown energy at a particular unknown initial angle. If the first ray interacts with the first stage 211, then the deposited energy $\Delta E1$, time and location of the first interaction 231 is measured, with whatever measurement error is involved. The remaining energy, if any, is emitted as a second ray 252 of longer wavelength. If the second ray 252 interacts with another stage, e.g., stage 212, then the deposited energy $\Delta E2$, time and location of the second interaction 232 is measured, with whatever measurement error is involved. The remaining energy, if any, is emitted as a third ray 253 with even longer wavelength. If the third ray 253 interacts with another stage, e.g., stage 213, then the deposited energy $\Delta E3$, time and location of the third interaction 233 is measured, with whatever measurement error is involved. Based on the angle between $1^{st}$ interaction 231 and second interaction 232, and the energy $\Delta E1$ deposited by the first interaction 231, the angle $\theta1$, and thus the cone 260 of potential source locations for the first ray 251, is determined. Based on the measurement errors, there is some uncertainty in the angle and position of the cone 260, but that uncertainty is ignored here for the purposes of illustration.

If most of the energy $E_0$ of the first ray 252 is absorbed in the three interactions 231, 232, 233, then an estimate of the value of $E_0$ is obtained by summing the energy deposited in the three interactions, that is $E_0 \approx \Delta E_1 + \Delta E_2 + \Delta E_3$. If not, or if the total energy is not known or reasonably estimated, then the value of $E_0$ can be inferred using Equation 2A, above.

From the kinematics of the Compton scattering process, the energy deposition and position data for each scatter of the high energy particle is used to determine the incident energy and the angle of incidence. But, as mentioned above, the scattering information does not determine the precise origin of the high energy emission, but instead the origin can be at any point on the surface of a cone, referred to as a cone of origin. The axis of the cone is the line connecting the first two scattering interactions 231 and 323, the cones apex is the first scattering location and the cone opening is the angle $2\theta_1$ where $\theta_1$ is the scattering angle and the angle between the cone axis and the cone surface. The scattering angle $\theta_1$ or angle $2\theta_1$ of the opening of the cone is determined from Equation 3, above, based on $E_0$ and $\Delta E_1$.

Although processes, equipment, and data structures are depicted in FIG. 1 and FIG. 2 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Of all the locations on the cone surface, only those locations within a particular target volume 291 inside the subject 290 are considered as viable possible positions for the source event. The target volume may be the entire volume of the subject. In some embodiments, the target volume is confined to a region where source events are expected, for example, within a predetermined distance of a cause, such as a proton beam or an implanted radioactive source. FIG. 3A is a block diagram that illustrates an example intersection of the surface of cone 260 of possible source positions within a target volume 291, according to an embodiment. The actual but unknown position 310 of the source event is depicted. The next problems are to infer the location of position 310, and then map all the event sources to create a 3D or 2D image of events in the target volume. In a previous approach called back propagation, multiple events are assumed to originate from the same location so that three cones from three different events are plotted on the same plane in the target volume and any point or region common to all three is taken as a source location. This approach gave unsatisfactory results that agreed poorly with known event source locations.

A more sophisticated approach in the prior art is called stochastic origins ensemble (SOE) iterative algorithm. This approach iterates to a more probable solution for the location of the source event by considering the locations of all the cones from a large number N of events. The set of N events and associated cones constitutes the ensemble. At the first iteration, a point on each cone is chosen at random. For example, initial random location 320 is selected on cone 260 in the target volume 291 in subject 290. The initial points on all N cones for all N events are used to generate a spatial histogram which is used as the basis for a probability density distribution. In the next iteration, an event cone is selected N times from the entire ensemble; and, for each event, a new random point is selected on the surface of cone 260 in the target volume 291. The probability of the previous location and the probability of the new location for each event cone are both determined based on the probability density distribution of the current iteration. If the new location has a higher probability, then it is used as the better location for the current event and replaces the old location for the current event and the probability distribution is updated to that which reflects the new event position on its cone. Otherwise the old location is kept; and, the new location is rejected. The process is repeated for a large number L of iterations or until convergence is reached, e.g., the probability density distribution does not change significantly between iterations. Any condition for convergence of the solution can be used in various embodiments, e.g., change in spread of the probability distribution, reaching L iterations, among others. When that condition is satisfied, the process stops.

FIG. 3B is a block diagram that illustrates an example iteration of stochastic origin ensemble (SOE) method for positioning events from spatially related sources, according to an embodiment. Cone 260, target volume 291, actual unknown location 310, and initial random location 320 are as described above for FIG. 3A. The random locations 330 on other cones inside the target volume from other source events are depicted as open circles and are used to generate a spatial probability density distribution using voxels and a histogram, as described below. Then a second random location 322 is selected on the cone. Based on the probability density distribution, the second random location 322 is more probable than the initial random location 320 and is taken as the better location on cone 260. The new location 322 is then used in a new probability density distribution during the next iteration.

Figure 3C:
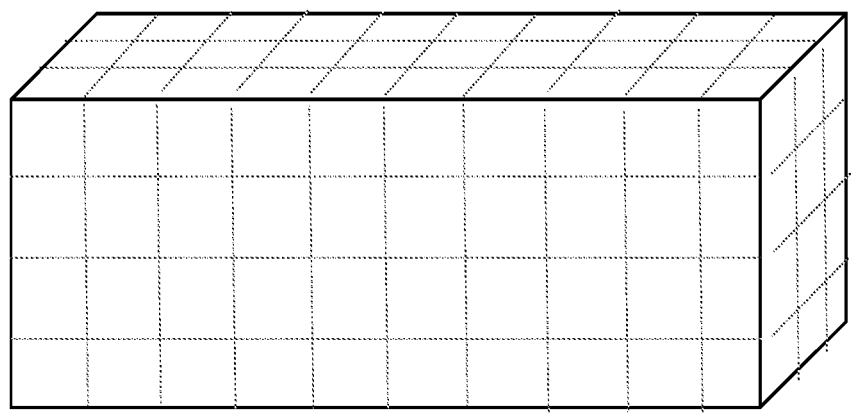
FIG. 3C is a block diagram that illustrates an example set of voxels having a target resolution in a subject volume, according to an embodiment.
Figure 3D:
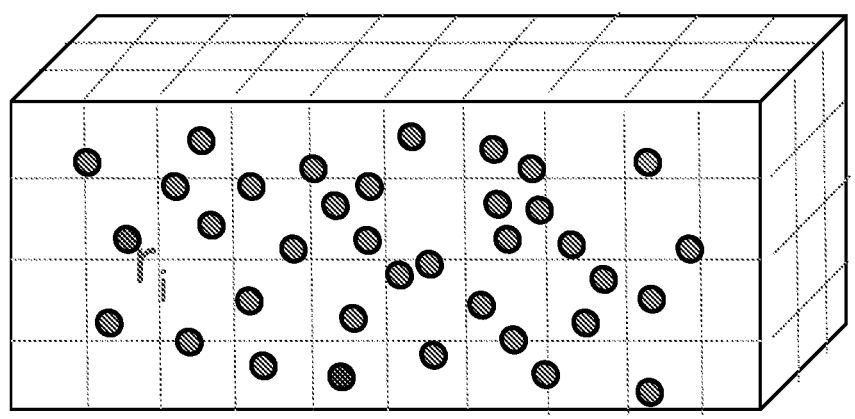
FIG. 3D is a block diagram that illustrates how selected positions of multiple source events populate a histogram of counts per voxel, according to an embodiment.

FIG. 3C is a block diagram that illustrates an example set of voxels having a target resolution in a subject volume, according to an embodiment. The target volume is divided into these volume elements (voxels) in order to produce a spatial histogram H of counts in each voxel that reflect the density distribution of events at each iteration. FIG. 3D is a block diagram that illustrates how selected positions of multiple source events populate a 3D spatial histogram H of counts per voxel, according to an embodiment. The location labeled ri indicates the location of the ith event in the current iteration. In some embodiments, its relative probability is based on the number of other events in the same voxel. Mathematically this is expressed as follows. For each cone i, choose a new random point βi on the surface of the cone and in the target volume. Compare the probability density ρ of ri, ρ(ri), based on the histogram H at this iteration to the probability density of βi, ρ(βi) based on the same histogram. For example, in the previous embodiment of the SOE, if the condition expressed by Equation 4A is satisfied, $$\frac{\rho(\beta i)}{\rho(ri)} > U(0, 1) \quad (4A)$$

where, U(0,1) indicates a random variable selected from a uniform probability distribution over the interval 0 to 1, then set ri=βi and ρ(ri)=ρ(βi). The test is relative to U(0,1) and not relative to 1 because sometimes the point is moved even if the probability goes down. This is allowed in order to avoid formation of local high density regions (hot spots) which can cause artifacts in the image. Otherwise leave ri and ρ(ri) unchanged. When bi is selected, the counts in the affected voxels of the histogram H are updated. Thus the method includes In a new embodiment presented here, to improve convergence, the contribution of the old location to the current voxel (1/N) is removed from the probability of the old location. In this embodiment, if the condition expressed by Equation 4B is satisfied, $$\frac{\rho(\beta i)}{\rho(ri) - \frac{1}{N}} > U(0, 1) \quad (4B)$$

then set ri=βi and ρ(ri)=ρ(βi). Otherwise leave ri and ρ(ri) unchanged. Thus, this embodiment includes updating for each source event during each iteration the selected location on the corresponding cone based at least in part on values of the counts in the histogram excluding the current source event.

The parameters of the algorithm are the number N of events and corresponding cones, the number M of iterations, and the size v of the voxels for the probability density distribution. The result is a 3D image of the locations of the different source events over an integration time long enough to detect N events, displayed as a projection in either one or two dimensions or in full three dimensions. In some embodiments, the initial energy $E_0$ of the source event is also determined and displayed on the image. For example, the dots representing each event are colored, or given greyscale shading, based on the initial energy $E_0$. In some embodiments, the image is computed and displayed again in a different overlapping or non-overlapping integration time interval.

Figure 4A:
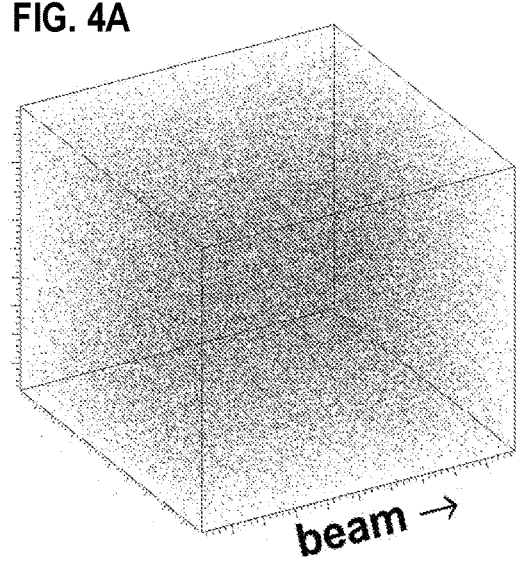
FIG. 4A through FIG. 4C are graphs that illustrates example maps of selected positions of multiple source events after various numbers of iterations of the SOE method, according to an embodiment.
Figure 4B:
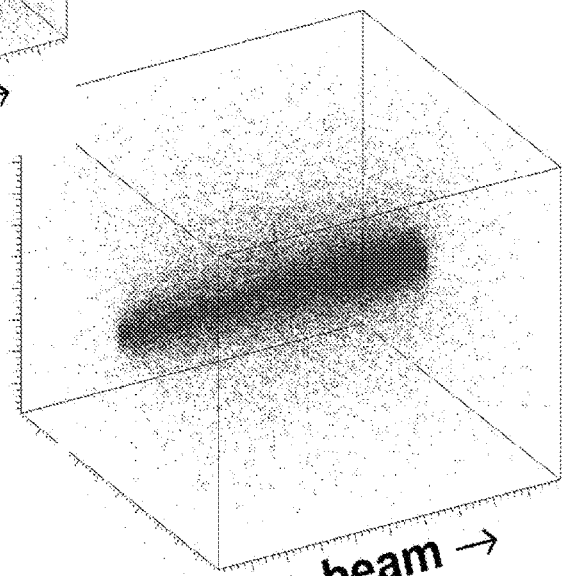
Figure 4C:
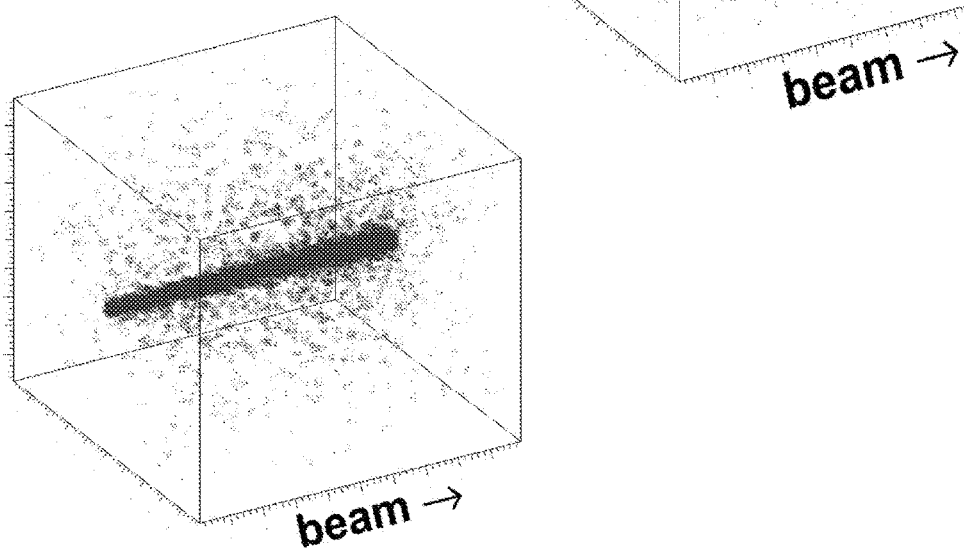

FIG. 4A through FIG. 4C are graphs that illustrates example maps (3D images presented in perspective) of selected positions of multiple source events after various numbers of iterations of the SOE method, according to an embodiment. This example was developed for a simulation of data received from a proton beam penetrating a volume of water. FIG. 4A depicts the distribution of initial locations for the source events, FIG. 4B depicts the distribution of locations of source events after 500 iterations, and FIG. 4C depicts the distribution of locations of source events after 80,000 iterations. As can be seen after 80,000 iterations the cloud of points suggests a proton beam interacting with the water molecules to generate gamma ray emission events distributed along the proton beam.

To improve convergence in fewer iterations, in some embodiments, the previous SOE algorithm is changed in one or more ways. The exclusion of the current location from the histogram, represented by Equation 4B discussed above, is one such improvement used in some embodiments. Another improvement is presented here.

In the previous approach, on each iteration, N cones are selected at random with replacement so that the same cone can be selected multiple times and some cones are not selected in some iterations. In one improvement embodiment, the cones are selected in random order but without replacement, so that each cone contributes once and only once to each iteration.

Figure 5A:
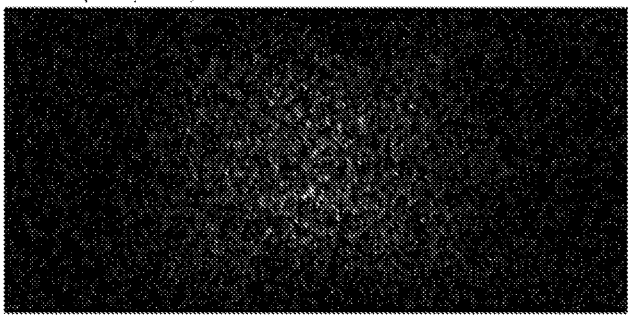
FIG. 5A through FIG. 5D are images that illustrates example averaging of three statistically independent solutions for the SOE method, according to an embodiment.
Figure 5B:
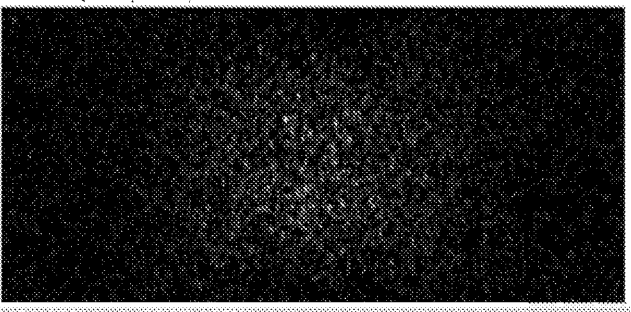
Figure 5C:
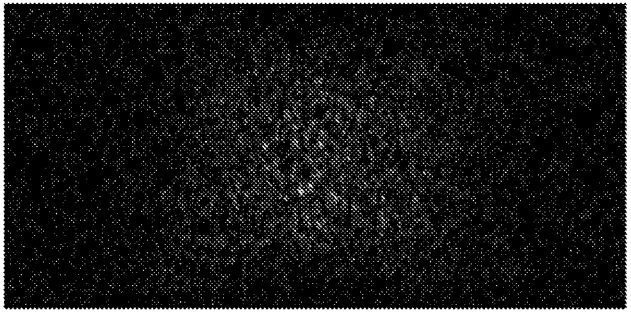
Figure 5D:
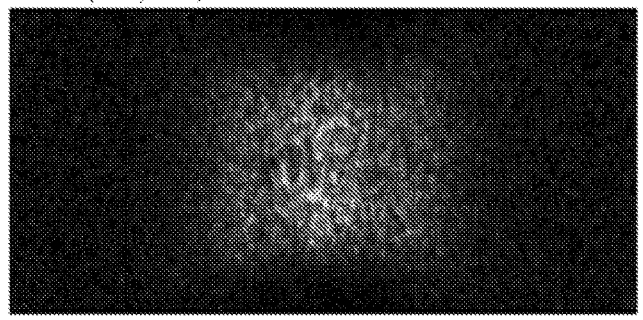

In a third improvement embodiment, the SOE algorithm is applied independently M different times to get M different locations for each cone, and the results from all M solutions are combined, e.g., by averaging the M locations for each cone obtained in the M different solutions. This is appropriate because each solution starts with a different set of randomly selected initial locations and each iteration selects the cones in random order. Thus the solutions are statistically independent. Averaging over statistically independent estimates reduces the error from that associated with each solution separately. In other embodiments, other combinations are performed, such as taking the average value inside a voxel or taking the root mean square of each coordinate. FIG. 5A through FIG. 5D are images that illustrate example averaging of three statistically independent solutions for the SOE method, according to an embodiment. The 3D locations for each cone are projected to a particular plane for display in a 2D image. FIG. 5A through FIG. 5C show the three independent solutions for the source events, while FIG. 5D show the average position of each cone for all cones, providing a tighter brighter distribution of event locations.

In some embodiments, other information is used to reduce the number of stages needed or to improve the selection of source event locations on the cones. For example, if the location of the center axis of a proton beam is known, or a centroid of an implanted radiation source is known, then the location selected on the cone can be the closest point on the cone in the target volume to the known axis of the proton beam or centroid of the implanted radiation source. FIG. 6 is a block diagram that illustrates an example closest location to a known gamma source on a cone of possible source positions, according to an embodiment. Cone 260, target volume 291, and initial random location 320 are as described above for FIG. 3A. The location of a center of the source events, such as the central axis of a proton beam or a centroid of a targeted organ from a concurrent or co-registered CT scan, is known. This is represented in FIG. 6 by the known proton beam or other source locations 630 in the target volume. In this example, the known locations 630 do not intersect the cone 260, but can still be used to find the location of a point 620 on the cone closest to the known locations 630. Thus, in this embodiment, the method includes receiving data indicating a set of one or more known positions in a target volume of a subject associated with a cause of a high energy particle source event. In such an embodiment, an initial location 620 on the cone is selected that is closest to the known source location in the target volume. In some embodiments, this closest approach method includes testing to see that the shortest distance between the cone surface and the source location is less than some preset value (e.g. closest point on cone is <1 cm away from source location. If this is true, then the event and its cone are kept to use in the reconstruction. If his condition is false, then the event and its cone are discarded and NOT used in the reconstruction. In some embodiments, the locations that pass this step are kept as the final solution.

In some embodiments, the SOE method is also used to refine the initial location 620 based on the closest approach. In such embodiments, all cones with distances to the source less than the preset value are taken for use in the SOE reconstruction or a maximum likelihood reconstruction or other stochastic reconstruction. These stochastic reconstruction acts as a filter to remove "bad" cones from the reconstruction and the result is more realistic images with less noise. The convergence is expected to occur faster and consequently the number L of iterations can be set smaller than in the other stochastic methods. In some embodiments, the SOE is used but with the proximity of the selected point to the known position serving as a basis for the probability density distribution. For example, given two points ri and βi on cone i during the current iteration, the one closer to the known position of the cause of the source event is taken to be more probable so it is kept while the other is discarded.

In some medical imaging embodiments, including PET and SPECT imaging, the source energy $E_0$ is estimated with only two interactions. Since such medical imaging uses low energy gammas (<1 MeV), in principle, only 2 interactions in one or two stages are enough to deposit the entire emitted energy. Thus one could image effectively using double scatter events. In some embodiments, the initial energy ($E_0$) of the ray used for medical imaging (e.g. 511 keV annihilation energy for PET) is already known, one just looks for and uses in the image production double scatter events where $\Delta E_1 + \Delta E_2 = E_0$ for the particular initial energy being used. This process ensures that the simultaneous events used are suitable and avoids the introduction of noise from spurious interactions not associated with real source events in the target volume.

In some embodiments using the closest approach to a known cause of the source events, the initial energy of a gamma ray can be determined for a two interaction event without needing all of the energy to be absorbed. This can be accomplished by the following method. In a first step, a guess of the initial energy is made. The assumed value is used to create a cone for the gamma and the shortest distance between the cone surface and the known source position is calculated. In a second step, a new guess at the initial energy is made and a new cone is created. The shortest distance between the new cone and the source position is calculated. In a third step, whichever of the two guesses at the initial energy gives the smallest distance between cone and source position is chosen as the initial energy of the gamma. If the gamma originates from a known radio-isotope, then the known gamma emission energies of the isotope are used for the initial guesses of the gamma energy. The known gamma emission that gives the shortest distance between cone and source position is chosen as the initial energy for that event. If the energy of the gamma emission is completely unknown, then a series of initial energy guesses can be made, with each subsequent guess increasing (or decreasing) the guessed energy value by a fixed amount. A cone is created for each initial energy guess and the shortest distance between cone and source position is determined. Effectively, this method scans over a set range of energy values. The energy value in the scanned range that gives the smallest distance between cone and source position is chosen as the initial energy for this event.

These approaches using a Compton camera and imaging techniques offers several advantages over typical PET imaging. The Compton camera apparatus is smaller; a large PET imager that takes up a whole room is not needed. Compton camera apparatus can be battery powered, making the apparatus portable. The Compton camera apparatus is cheaper than a PET or SPECT imager by about a factor of 10 (or more). The Compton camera apparatus can be used to measure and image a large range of gamma energies from 100 keV up to 10 MeV. As shown by this example, a Compton camera apparatus can be configured and used for a wide range of nuclear imaging and functional imaging applications.

2. METHOD

Figure 7:
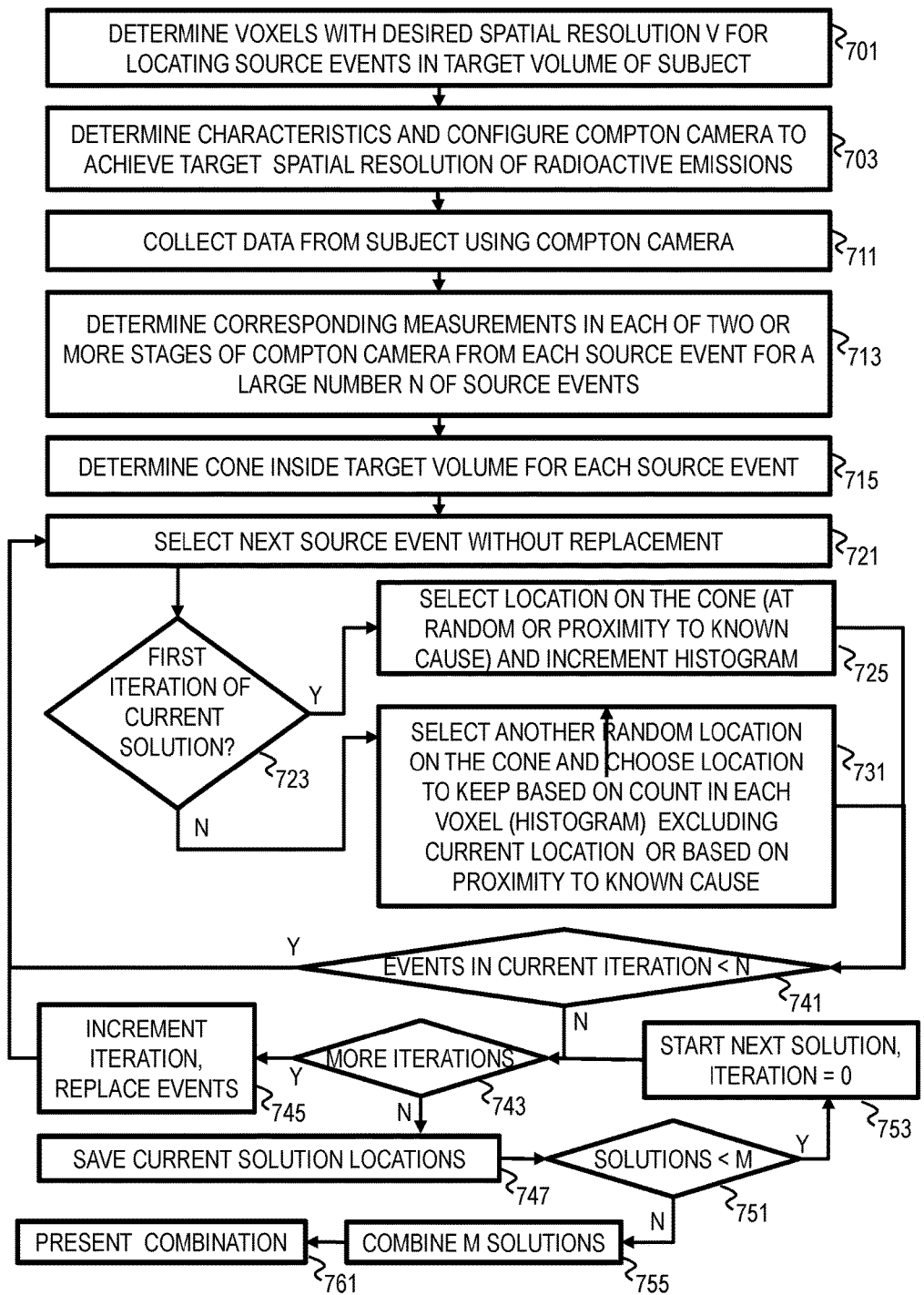
FIG. 7 is a flow chart that illustrates an example method for producing an image of source event locations, according to an embodiment.

FIG. 7 is a flow chart that illustrates an example method for producing an image of source event locations, according to an embodiment. Although steps are depicted in FIG. 7 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 701, the target spatial resolution v is determined for locating events in a target volume within a subject that is susceptible to internal radioactive emissions. The subject can be any human or animal or other living or dead organism, or any man-made or natural inanimate object, such as a machine, a building or a geological formation. The radioactive emission may be natural or artificially implanted, such as radioactive ore in a geological formation, spillage from a machine that uses or is powered by nuclear material, radioactive tracers used to detect movement of contaminants or fluids through the environment, or radioactive sources introduced into a subject for diagnosis or treatment. The target volume is the portion of the subject within which the radioactive emission are of interest, such as the volume in the vicinity of a proton beam used in therapy. The target resolution depends on the use for the information. For example, in detecting the Bragg peak absorption of the proton beam within a target tissue, a resolution of a few millimeters may be desirable; while, for detecting ore in a geological formation, a resolution of a hundred meters may be advantageous. The target resolution is used to determine the size of voxels in the target volume for accumulating counts of emission events to use as a probability density distribution in some statistical methods, such as the stochastic origins ensemble (SOE) method described above. In such embodiments, step 701 includes breaking the target volume up into volume elements (voxels) of size on the order of the target resolution v. In some embodiments that do not use the SOE method, step 701 is omitted.

In step 703, the characteristics of a Compton camera suitable for the target volume and spatial resolution v are determined and a suitable Compton camera is procured. In some embodiments, step 703 includes designing the Compton camera (including some or all of the number and spatial arrangement of stages and the number and type of detectors in each stage) for a particular purpose and building the stages or camera or causing the stages or camera to be built. For example, in a pilot study of the feasibility of using Compton cameras to detect absorption of a proton beam, a commercially available Compton camera was used that was suitable for a feasibility study but not optimal for that particular purpose. A Camera designed for proton beam absorption in human tissue, would have distinctive characteristics not available in other cameras or suggested by other uses. For example, for millimeter resolution in a human body of 1 meter size, the Compton camera stages, necessarily placed a meter from the source, would advantageously have detectors capable of measurements with millimeter to centimeter resolution and ranges of photon energy (wavelength or frequency) interaction suitable for the prompt gamma emissions that result from the absorption of the proton beam in the subject's tissues. In some embodiments, step 703 includes steps to select or build a suitable Compton camera for an intended purpose.

Figure 8:
FIG. 8 is a photograph that illustrates an example Polaris-J Compton camera, used in some embodiments.

For example, in some embodiments a Polaris-J Compton camera was used that was originally designed for low energy (<2 MeV) gamma imaging. FIG. 8 is a photograph that illustrates an example Polaris-J Compton camera. There are four stages 801, 802, 803 and 804. Each stage contains a 2×2 array of pixelated Cadnium Zinc Telluride (CZT) crystals (2 cm×2 cm×1.5 cm each) for a total CZT area of 4 cm×4 cm. For this prototype, CZT was chosen for its high interaction cross section for gamma rays in a range of interest (up to 117 MeV). All detector crystals are pixelated 11×11 in x- and y-directions on the anode with a planar cathode. Using pulse height and shape analysis of the anode signals, a resolution of 1.5 mm is achievable in the x- and y-directions, and <1 mm in the z-direction (depth). The individual stages are linked electronically through a synchronization coincidence timing (SCT) module 810, allowing the user to determine the number of stages that must have recorded a gamma interaction within a fixed 1.5 µs coincidence time interval in order to trigger a full readout and reset of all stages of the Polaris-J CC, the reader is referred to McCleskey et al. (2015) and for a description of the readout electronics the reader is referred to Zhang and He (2006).

For proton beam imaging and PET imaging it is advantageous to have a large enough defector array (surface area) to allow a 3D image to be acquired with Compton imaging technique. This provides sufficient parallax with the camera to get a 3D image of the full proton beam. Also the detector needs to be able to detect gammas in a short window of time when the proton beam is on or before the PET tracer decays or is washed out in the body. Thus, it was determined that the detection efficiency of the Polaris-J was too low to be clinically useful. Therefore it was determined to make two changes to the next generation prototype camera to improve the detection efficiency. First, the size of the CZT detector array was increased to 4 cm×16 cm (e.g., a 2 by 8 array of crystal, each crystal being a 2 cm by 2 cm by 1.5 cm CZT crystal). Second the day readout circuits were switched to a faster model to improve the achievable count rate to about 50,000 counts/sec. The newly designed camera is currently under construction.

In step 711, data are collected that indicate measurements by the Compton camera of emissions from the subject. The collected data includes time of interaction, location within stage (e.g., location in detector and detector identifier or position) and energy deposited. In some embodiments, the data collected includes the coordinates of the interaction in the system coordinates, for example with an origin in or close to the target volume in the subject.

In step 713, interactions associated with one source event are determined. In some embodiments, step 713 includes determining coincident interactions in multiple detectors in one or more stages that are likely due to the same source event in the subject. For example, an interaction detected in stage one starts a coincident time interval during which subsequent interactions detected in one or more other detectors or stages are considered candidate second and subsequent interactions downstream of the initial interaction. In some embodiments, the candidate interactions are screened to eliminate those unlikely due to the same source event. For example, candidates are eliminated if they produce a cone that does not intersect the target volume. In some embodiments with smaller energy emissions or emission of a known energy, only a one or two stage Compton camera is used and candidates are eliminated if the sum of the two deposited energies does not closely equal the known energy of the ray emitted by the known source type. In some embodiments in which the locations of the cause of the source events is known, but the energy is not, the initial energy can be determined using the one energy, among a range of scanned energies, which produces a cone for which the closest approach to the known position is best, as described above. As a result of step 713, a large number (N) of events are identified in the collected data. Each event involves two or more interactions (each interaction characterized by time, location, deposited energy) in corresponding detectors in one or more stages of the Compton camera within a coincident time interval. Thus, step 713 includes collecting from each of a plurality of detectors in one or more stages of a Compton camera within a coincidence time interval, location and deposited energy from an interaction associated with a single source event in the target volume of the subject.

In step 715, a surface of a cone of possible source locations, e.g., the cone of possible origins, is determined for each of the N events. In some embodiments, the total energy of the source event, $E_0$, is also estimated for each of the N events, based on the energy deposited in all the interactions associated with the event in various detectors of the Compton camera, or $\Delta E_1$, $\Delta E_2$ and Equation 2A. Thus, step 713 includes determining for the source event a cone of possible locations for the source event based on the locations and deposited energies collected from the plurality of detectors in one or more stages of the Compton camera.

Step 721 starts a loop through N events, by selecting the next source event, either sequentially or at random from all the N source events. The loop through all events is repeated in some embodiments for multiple iterations, with L representing the number of iterations. In a previous description of the SOE, the events are chosen at random with replacement. Thus, when choosing each of N events, some events are selected more than once during one iteration while other events are skipped altogether in the iteration. In various embodiments of the claimed invention, the order of events is chosen either sequentially or at random but without replacement, as depicted in FIG. 7, so that all N events are selected during each iteration. Thus, in some embodiments, the plurality of N source events is used once without replacement as the current source event, during each iteration of the L iterations. In other embodiments with other novel features, step 721 is replaced by the previous method of selecting the next of N events with replacement.

In step 723, it is determined whether this is the first iteration through the N events. If so, control passes to step 735. In non-iterative methods, such as some embodiments based on closest approach to a known position, there is only one iteration, i.e., the first iteration.

In step 725, a position on the cone is selected at random as in the standard SOE approach (thus step 725 includes, in some embodiments, selecting for each source event a random location on the cone of possible locations for a corresponding source event), or, in some embodiments, based on proximity to the known cause of the emission event, e.g., the axis of the proton beam or centroid of the PET or SPECT source. In embodiments that use a histogram of count of locations in each voxel as a probability density distribution, like an improved SOE method, the voxel including the selected location is incremented. Thus, in such embodiments, step 725 includes generating a histogram that indicates, for each voxel, a count of the selected locations that occur inside the voxel. In embodiments where a different measure of location "goodness" is used, e.g., proximity to a known cause of the emissions, the histogram is not used; and, no voxel has its count incremented. Control then passes to step 741.

In step 741, it is determined whether there are any more events to process during the current iteration, e.g., if the number of events processed is less than N. If so, then control passes to back to step 721 to select the next event to process. If not, then control passes to step 743 and following, described below, to determine if there are any more iterations to be taken before a solution is accepted. Again if an iterative process is not used, then the number of iterations is complete, e.g., L=1.

If it is determined, in step 723 above, that this is not the first iteration through the N events, then control passes to step 731. In step 731, another random location is selected on the surface of the cone and inside the target volume. The goodness of both locations is compared and the better location is retained. In the previous SOE, the goodness is based on the counts of locations in the voxel containing the location, using Equation 4A. In an improved method developed here that is expected to lead to faster convergence, the contribution to the voxel count by the current location is removed, e.g., using Equation 4B above. In another embodiment, the goodness is based on proximity to a known location of the cause of the emissions, such as the axis of the proton beam or the centroid of the radioactive source used in PET or SPECT scans. The location closer to a known location of the cause of the emission is chosen as the current location for the event. Thus, in some embodiments, step 723 includes selecting a particular location on the cone within the target volume based on proximity to the set of one or more known positions in the target volume Control then passes to step 741.

As described above, in step 741, it is determined whether there are any more events to process during the current iteration, e.g., if the number of events processed is less than N. If so, then control passes to back to step 721 to select the next event to process. If not, then control passes to step 743.

In step 743, it is determined whether there are any more iterations. For example, if it is predetermined to perform a large number L of iterations, then it is determined if the number of iterations so far performed is less than L. If so, then control passes to step 745. In another embodiment, it is determined whether enough iterations have been performed based on whether some other convergence conditions is satisfied, e.g., the spread of locations is not reduced between successive iterations. For example, if the spread of locations reduced by at least a threshold amount, then the convergence condition has not been satisfied, and another iteration is to be performed. As another example, a count is kept of the number of cones for which the point of the cone was moved. If the percentage of cones with moved points is less than a threshold (e.g., 1%) then the condition for convergence is satisfied and the reconstruction for this solution instance is stopped. Control passes to step 745.

In step 745, the number of iterations performed is incremented, and all events are replaced, that is all events are available for selection of the next event. Control passes back to step 721 to loop through N events for the next iteration.

If it is determined in step 743 that there are NOT any more iterations, then, in step 747, the current set of N locations for the N events are saved as the solution set of locations. Thus, the loop over L iterations over the N events includes determining a solution comprising a set of N solution locations for the N source events from the SOE iterative algorithm after L iterations by updating for each source event during each iteration the selected location on the corresponding cone based at least in part on values of the counts in the histogram, and updating the histogram based on the updated selected location for each source event during each iteration.

In some embodiments, the one solution set is enough. However, according to some embodiments, M different solution sets are desired. In this embodiment, M statistically independent solution sets are determined. A statistically independent solution set is obtained by initiating the process with a different set of random locations. In these embodiments, step 747 passes control to step 751.

In step 751, it is determined whether the number of solution sets is less than the target number M. If so, then another solution set is needed; and, control passes to step 753.

In step 753. The next solution is started by setting the number of iterations completed to zero, or otherwise setting the convergence conditions to "not satisfied;" and, sending control back to step 743 described above. Thus, in some embodiments, steps are repeated for a plurality of M instances of the SOE iterative algorithm by selecting for each source event M different random locations on the cone to initiate the plurality of M instances and to determine a plurality of M instances of a solution.

If it is determined in step 751 that the number of solution sets is NOT less than the target number M, i.e., that M solution sets have been obtained, then control passes to step 755. In step 755, the M solution sets are combined, by combining the M values for the location for each event. In some embodiments, the combination is determined by computing an average x, y and z coordinate of the M locations for each event. In other embodiments, other combinations are used. For example, in some embodiments, the median x, y and z values are used of the M locations for each event. In some embodiments, all M points for each event are plotted on the same image. [Thus step 755 includes combining the plurality of M instances of the solution location for each source event to determine a combined solution location for each of the N source events. Control then passes to step 761.

In embodiments in which one solution is sufficient, steps 751, 753, 753 and 755 are executed with M=1, or steps 751, 753, 753 and 755 are omitted and control passes directly from step 747 to step 761.

In step 761, data is presented on a display device based on at least one location from the final (one or combined) solution set for a corresponding event. For example, data is presented on a computer display device such as a monitor or printer. The data can be a listing of one or more locations in the one or combined solution set, a graph of one or more locations of the one or combined solution set, a 2D image of one or more locations of the one or combined solution set, an image in which the color or greyscale represents the initial energy $E_0$ of a point representing a location. In some embodiments, the display device is another device that uses the information from the combined solution set, such as a proton beam generator that uses the information from the locations to determine to continue to fire a proton beam or to stop based on determining that a sufficient or insufficient dose has been delivered to a target tissue or that an excessive dose has or has not yet been delivered to an non-target organ at risk, or that a dose is being delivered incorrectly by any other measure. Thus step 761 includes presenting, on a display device, data indicating the particular location in the target volume.

Figure 9:
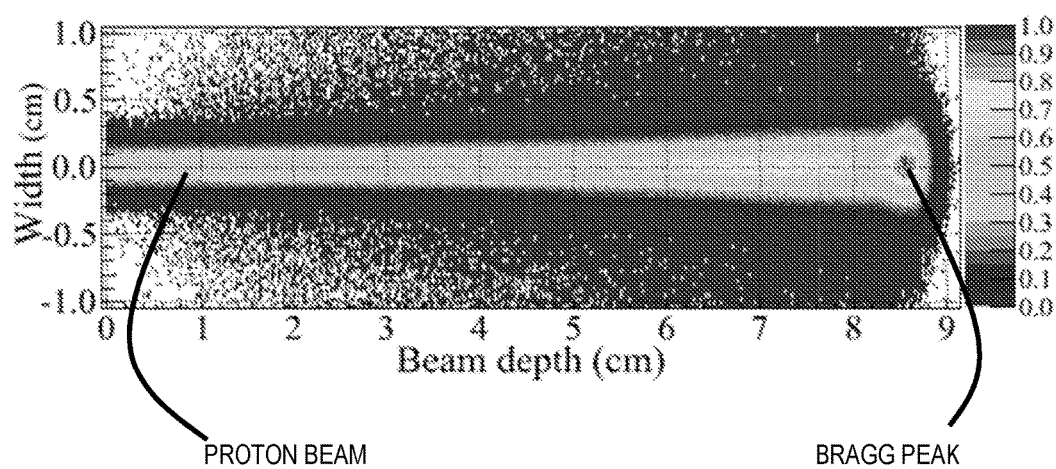
FIG. 9 is an image that illustrates an example simulated image in which each emission event contributes a color to a corresponding pixel based on the initial emission energy, E0, according to an embodiment.

FIG. 9 is an image that illustrates an example simulated image in which each emission event contributes a color to a corresponding pixel based on the initial emission energy, E0, according to an embodiment. The horizontal axis indicates distance in the target volume along the z axis of FIG. 2 and the vertical axis indicates distance in the target volume along the x axis of FIG. 2. The proton beam and Bragg peak where the most energy is concentrated are clearly evident from the emission of prompt gamma rays detected by a simulated Compton camera.

3. EXAMPLE EMBODIMENTS

Example embodiments include demonstrating the techniques for proton beam therapy, PET imagery and SPECT imagery. An advantage of the method as applied to PET and SPECT, among others, is that gamma rays emitted by radioactive tracers have a single energy which is generally known (e.g. 511 keV for PRT tracers used with FUG) whereas gamma rays emitted as a result of proton beam interaction with the tissue have a wide spectrum of energies.

3.1 Proton Beam

In some embodiments, the interactions of a proton beams with human tissue, or phantoms for such tissues, are determined. For in-vivo range verification, adequate data to allow for localization of the beam range to within 1 to 2 mm is most advantageously collected during the delivery of only a fraction (for instance ≤20%) of the dose delivered for each treatment field of a daily treatment. This gives an operator of the proton beam enough time to cut off the therapy if the early returns indicate a misplaced beam or Bragg peak before too much damage is sustained by the surrounding organs not being targeted by the therapy. For standard proton therapy fractionation schemes, as simulated hereinbelow, this means the goal for prompt gamma range verification would be to produce images with delivery of only about 25 centiGray (cGy. 1 cGy=1×10$^{-2}$ Gray, a Gray is a radiation absorbed dose measurement unit). 25 cGy is about equal to 4.5×10$^7$ protons.

To address such uses, input data has been generated to test the improved, SOE-based reconstruction code by using a previously developed Monte Carlo (MC) model that simulates Compton camera (CC) measurements of characteristic prompt gamma (PG) emission from tissue irradiated with a proton pencil beam (Peterson et al 2010). In the following, the MC model and the SOE implementation is described as an example embodiment.

To generate the secondary gamma input data, inventor has used an MC model developed with the Geant4 (version 9.4 patch 1) toolkit (Agostinelli et al 2003), as previously used and described by Peterson et al (2010) and Robertson et al (2011). The model consists of a clinical proton beam irradiating a tissue phantom with a three-stage CC positioned above it to measure the production of secondary gammas. The model includes a 110 MeV proton pencil beam with a Gaussian spatial profile (σ=1 mm) irradiating a 10×10×10 cm$^3$ soft tissue phantom with composition and density as defined by ICRU Report 49 (1993).

The MC model tracks secondary gammas (CP and PA) produced by nuclear scattering between the proton beam and nuclei in the tissue phantom. When any of these gammas sequentially Compton scatter in the first and second detector stages, followed by a Compton scatter or photoelectric absorption in the third stage, the MC model records the position (xi, yi, zi) and energy deposition (Ei) in each detector stage in an output file. Along with the scattering information, the model records the gamma's initial energy (or "true" energy) and the location at which it was emitted (or "true" origin). The object of the reconstruction is to closely emulate the distribution made up of the true initial energy and true location of multiple emission events.

The recorded gamma interaction positions and energy depositions in the CC are used to calculate the initial energy of the gamma ($E_0$) using Equation 2A. After $E_0$ has been calculated, the initial scattering angle θ1 is calculated using the Compton scattering formula in Equation 3. The detector uncertainties, such as position resolution, energy resolution, and Doppler broadening, are not included in the MC model. Therefore, unless the gamma scatters before reaching the detector, the calculated value for $E_0$ and the true energy (recorded by the MC model) will be equal.

When a calculation was completed with the MC model, the recorded position and energy deposition of each gamma scatter in the CC, along with the calculated values of $E_0$ and $\theta 1$, were output using ROOT, a C++ based data analysis package (Brun et al. 1997). In addition, the true origin of each gamma was included in the ROOT output file so that the SOE reconstructed images could be compared with the MC true origin distributions in the irradiated phantom.

In this example, the algorithm was terminated after 100,000 iterations (L=100,000) The size v of the voxels used is an algorithm parameter referenced her as the voxel probability parameter (VPP). The pseudo-random numbers used for random selections were generated using a combined Tausworthe generator (L'Ecuyer 1996) implemented in the ROOT package. For this implementation of the SOE algorithm, it is desirable that the pseudo-random numbers be equidistributed but not necessarily unique; they are used in different ways and with millions of origin cones which already have unique characteristics. The combined Tausworthe generator is maximally equidistributed and relatively fast. An array of 10000019 uniform random numbers between [0, 1) were generated and numbers were drawn as needed from the list, in order to improve the performance of the algorithm. To improve convergence, Equation 4B was used to subtract the current location from the histogram, and the N events on each iteration were selected without replacement, as described above. In most cases, using Equation 4B does not produce a significant difference. However, it was found that this improvement to the SOE algorithm is much less likely to move the representative position from a position with a larger probability to a position with a smaller probability, thus allowing the SOE calculation to converge faster and more completely. It was also found that stepping sequentially through the list of detected gammas and ensuring that each gamma is tested once for each iteration improves the convergence of the algorithm.

After the predefined number of iterations, the SOE algorithm records the 3D coordinates of the final representative position of each detected gamma. In some embodiments, the "final images" of the gamma emission are then constructed by binning the final 3D coordinates according to the desired image resolution, which may be smaller than the voxel resolution for the histogram. Therefore, the resolution of the final images is not determined by the size v of the origins histogram voxels used by the SOE algorithm. However, the quality of the final images may be affected by the VPP value. Using a smaller value for the VPP and, therefore, smaller voxels for the origins histogram, may improve the resolution of the reconstructed images. However, using a smaller VPP (i.e. smaller histogram voxels) means there are more voxels in the image field of view (FOV), which in turn means that more detected gammas are needed to fill these voxels and overcome the statistical noise in the origins histogram. To test these effects, the SOE algorithm was run with the input data containing 1 million (1 M) and 4 million (4 M) detected gammas using VPP values of 0.5 mm$^3$, 1.0 mm$^3$, and 2.0 mm$^3$. These numbers of gammas were chosen on the basis of previous studies, which estimated the number of triple-scattered gammas that can be measured by a CC in a clinical setting to be between 1 M and 4 M (Peterson et al 2010).

Results show that the SOE algorithm as modified above can be used to reconstruct clinically useful images (with a precision of 1 mm or better) of the secondary gamma emission produced during proton pencil beam therapy. Visual comparison of the SOE reconstructed and the true MC origin images shows good agreement in the plane parallel to the CC detector stages. On the basis of the results in the above study, it is concluded that (1) the SOE algorithm is an effective method for reconstructing images of a proton pencil beam from the data collected by an ideal CC and (2) the images produced by the SOE algorithm accurately model the distal falloff of secondary gamma emission during proton irradiation. In this study, the images predicted the distal falloff depths to within 0.6 mm$^3$. When CC detector position and energy uncertainties are included, the number of gammas required is likely to increase. However, further improvements to the algorithm, described above, such as the use of M independent solutions, may compensate for some of these effects. Thus, in this embodiment, the source event is a gamma ray emission and the cause of the source event is a proton beam interacting with an atom in the subject.

To detect the image with only about 20% of the dose delivered would mean increasing the prompt gamma detection efficiency of the prototype Compton camera from about 100 prompt gamma rays per cGy up to about 2500 prompt gamma rays per cGy.

The embodiment using M statistically independent solutions can help improve the image signal-to-noise ratio. Further, the embodiment may be significantly more suitable than the SOE alone for processing images acquired from a much smaller set of measured gammas (e.g., with the first 20% of the prescribed dose). Due to the random iterative process employed by the SOE method, the final position of each gamma in each of the M images will be statistically independent. Each image is of the same object (the gamma emission) and, thus, the final pixel values in the region of the PG emission will be very similar for each solution. In contrast, the final statistical noise patterns introduced by the method in each image will be independent of all other images. By summing (or averaging) the corresponding pixel values of all M images, the pixel values for objects (PG emission) in the image will increase by a factor of M (the number of independent images used), however the statistical noise patterns will only increase by a factor $\sqrt{M}$, thus effectively reducing the effects of noise in the image, and producing a final image with a greater signal-to-noise ratio.

3.2 PET Source

In some embodiment, the Compton camera and method is used as a substitute for more expensive and complex positron emission tomography (PET) imaging. PET is an important and widely used medical imaging technique that produces three-dimensional images of functional processes in the body. PET is used in clinical oncology, for clinical diagnosis of certain brain diseases such as those causing various types of dementia, and as a research tool for mapping human brain and heart function. PET imaging is particularly useful for imaging various processes taking place inside the brain of a patient. The system detects pairs of gamma rays emitted indirectly by a positron-emitting radionuclide (tracer), which is introduced into the body on a biologically active molecule. Upon contact with an electron, the positron is annihilated and the energy is emitted as a pair of oppositely propagating gamma rays. Three-dimensional images of tracer concentration within the body are then constructed by computer analysis. If the biologically active molecule chosen for PET is fluorodeoxyglucose (FDG), an analogue of glucose, the concentrations of tracer imaged will indicate tissue metabolic activity as it corresponds to the regional glucose uptake. Use of this tracer to explore the possibility of cancer metastasis (e.g, spreading to other sites or tissues) is the most common type of PET scan in standard medical care (e.g., is used in about 90% of current scans).

The energy of the gamma rays emitted by the FDG is 511 keV. On a minority basis, many other radioactive tracers are used in PET to image the tissue concentration of other types of molecules of interest. Each radioactive tracer emits gamma rays having a specific energy (may be different from 511 keV).

PET imaging determines the spatial distribution/position of the tracers emitting the pairs of gamma rays by determining coincident pairs of gamma rays emitted in almost opposite directions. The coincident pair of gamma rays determine a "line of response" (LOR) corresponding to each pair. The LORs are then used to reconstruct the spatial distribution and concentration of the radioactive tracer. A conventional PET scanner includes a plurality of detectors arranged in a ring around the imaged volume. One of the major shortcomings of the PET has to do with the high costs (both of the apparatus and of the operation) associated with the conventional PET scanner.

Two-stage CCs have low efficiency for gammas with energy greater than about 1 MeV, so Kurfess et al (2000) suggested the use of three-stage CCs that do not require the gammas to be completely absorbed. However, one-stage or two-stage CCs may be suitable for imaging applications of low-energy gamma rays emitted by many tracers used in PET imaging, such as the 511 keV gamma emitted by the tracer fixed to FDG. In a two-stage CCs, for a "double scatter" event, the gamma ray Compton scatters in the first stage and is photo-absorbed in the second stage. $E_0$ is determined using just the two deposited energies $\Delta E_1$ and $\Delta E_2$ Equation 2B; and, the cone angle $\theta 1$ is determined using Equation 3.

The target volume is chosen to include a spatial distribution of radioactive tracers/isotopes emitting gamma rays. The distribution of radioactive tracers inside a patient is a result of administering to the patient a biologically active molecule, such as FDG. The Compton camera is disposed to detect the gamma rays emitted by the radioactive tracers/isotopes inside the target volume. Thus in this embodiment, the source event is a gamma ray emission and the cause of the source event is a positron-emitting radionuclide as used in positron emission tomography (PET) medical imaging.

Because the initial energy ($E_0$) of the isotope used for medical imaging (e.g. 511 keV for PET) is already known, the data collected from the Compton camera data is preprocessed, in some embodiments, to select only double scatter events where $\Delta E_1 + \Delta E_2 = E_0$ for the particular radioisotope used, such as 511 keV. Thus, in some embodiments, the method includes selecting from each of only two detectors in one or more stages of the Compton camera within the coincidence time interval, location and deposited energy wherein a sum of the deposited energies in the two detectors is about equal to an energy of a gamma ray emitted by annihilation of the positron produced by the positron-emitting radionuclide.

3.3 SPECT Source

In some embodiment, the Compton camera and method is used as a substitute for more expensive and complex single-photon emission computed tomography (SPECT) imaging. The technique requires delivery of a gamma-emitting radioisotope (also called a radionuclide) into the living subject, normally through injection into the bloodstream. I A marker radioisotope is attached to a specific ligand to create a radioligand, whose properties bind it to certain types of tissues. This marriage allows the combination of ligand and radiopharmaceutical to be carried and bound to a place of interest in the body, where the ligand concentration is seen by a gamma camera. In some embodiments, the radio radionuclide is a soluble dissolved ion, such as an isotope of gallium(III).

SPECT imaging is performed by using a gamma camera to acquire multiple 2-D images (also called projections), from multiple angles. A computer is then used to apply a tomographic reconstruction algorithm to the multiple projections, yielding a 3-D data set. This data set may then be manipulated to show thin slices along any chosen axis of the body, similar to those obtained from other tomographic techniques. SPECT is similar to PET in its use of radioactive tracer material and detection of gamma rays. In contrast with PET, however, the tracers used in SPECT emit gamma radiation that is measured directly, whereas PET tracers emit positrons that annihilate with electrons up to a few millimeters away, causing two gamma photons to be emitted in opposite directions. A PET scanner detects these emissions "coincident" in time, which provides more radiation event localization information and, thus, higher spatial resolution images than SPECT (which has about 1 cm resolution). SPECT scans, however, are significantly less expensive than PET scans, in part because they are able to use longer-lived more easily obtained radioisotopes than PET.

Thus use of a Compton camera for a SPECT radionuclide imaging is directly analogous to the use for PET imaging. If the radionuclide gamma emission energy is low enough, a two stage Compton camera may suffice, as described above. Thus, in this embodiment, the source event is a gamma ray emission and the cause of the source event is a gamma-emitting radioisotope as used in single-photon emission computed tomography (SPECT) medical imaging.

4. COMPUTATIONAL HARDWARE OVERVIEW

Figure 10:
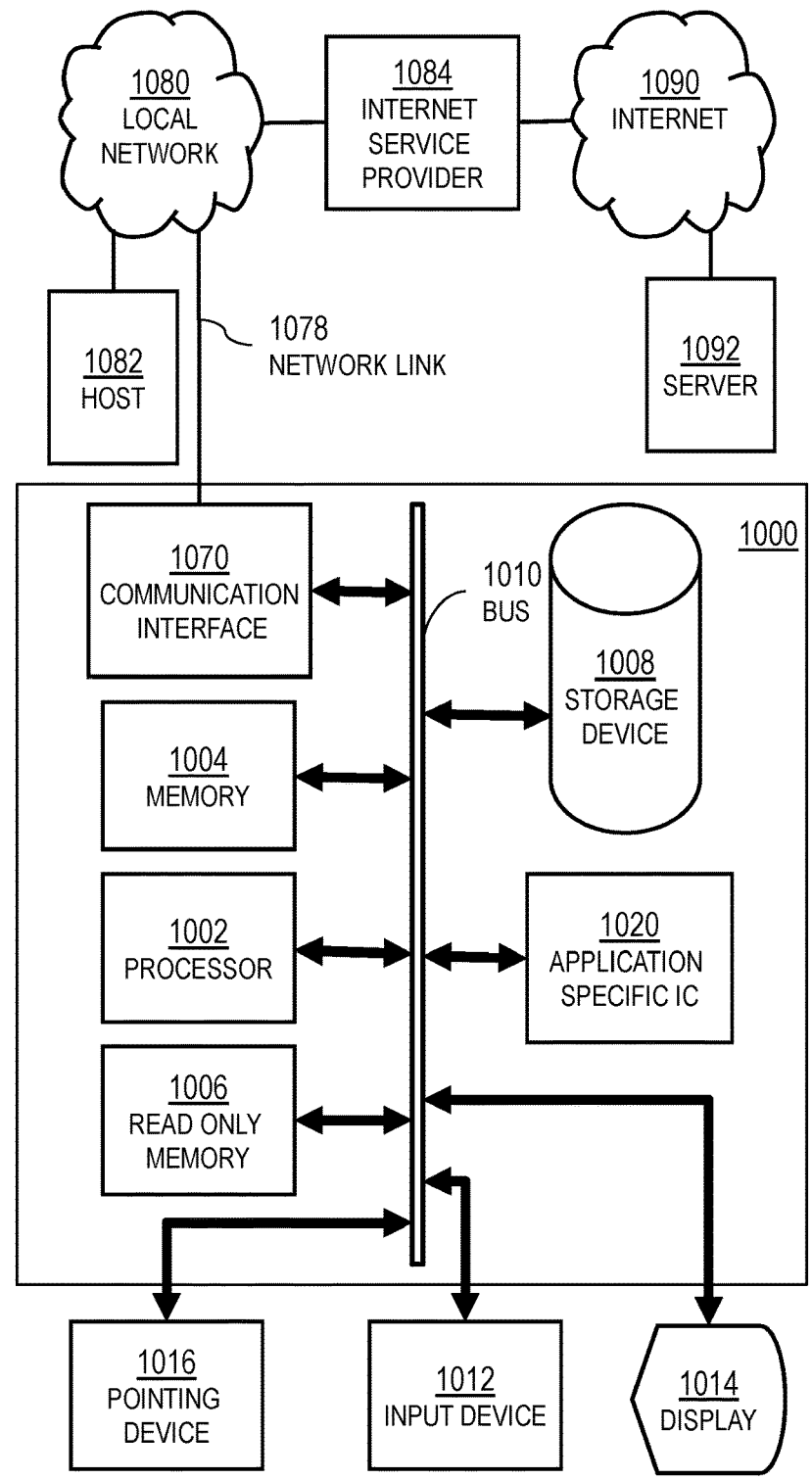
FIG. 10 is a block diagram that illustrates a computer system upon which an embodiment of the invention may be implemented.

FIG. 10 is a block diagram that illustrates a computer system 1000 upon which an embodiment of the invention may be implemented. Computer system 1000 includes a communication mechanism such as a bus 1010 for passing information between other internal and external components of the computer system 1000. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of one or more methods described herein.

A sequence of binary digits constitutes digital data that is used to represent a number or code for a character. A bus 1010 includes many parallel conductors of information so that information is transferred quickly among devices coupled to the bus 1010. One or more processors 1002 for processing information are coupled with the bus 1010. A processor 1002 performs a set of operations on information. The set of operations include bringing information in from the bus 1010 and placing information on the bus 1010. The set of operations also typically include comparing two or more units of information, shifting positions of units of information, and combining two or more units of information, such as by addition or multiplication. A sequence of operations to be executed by the processor 1002 constitutes computer instructions.

Computer system 1000 also includes a memory 1004 coupled to bus 1010. The memory 1004, such as a random access memory (RAM) or other dynamic storage device, stores information including computer instructions. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of computer instructions. The computer system 1000 also includes a read only memory (ROM) 1006 or other static storage device coupled to the bus 1010 for storing static information, including instructions, that is not changed by the computer system 1000. Also coupled to bus 1010 is a non-volatile (persistent) storage device 1008, such as a magnetic disk or optical disk, for storing information, including instructions, that persists even when the computer system 1000 is turned off or otherwise loses power.

Information, including instructions, is provided to the bus 1010 for use by the processor from an external input device 1012, such as a keyboard containing alphanumeric keys operated by a human user, or a sensor. A sensor detects conditions in its vicinity and transforms those detections into signals compatible with the signals used to represent information in computer system 1000. Other external devices coupled to bus 1010, used primarily for interacting with humans, include a display device 1014, such as a cathode ray tube (CRT) or a liquid crystal display (LCD), for presenting images, and a pointing device 1016, such as a mouse or a trackball or cursor direction keys, for controlling a position of a small cursor image presented on the display 1014 and issuing commands associated with graphical elements presented on the display 1014.

In the illustrated embodiment, special purpose hardware, such as an application specific integrated circuit (IC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1070 sends and receives electrical, acoustic or electromagnetic signals, including infrared and optical signals, which carry information streams, such as digital data.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1002, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1002, except for carrier waves and other signals.

Logic encoded in one or more tangible media includes one or both of processor instructions on a computer-readable storage media and special purpose hardware, such as ASIC 1020.

Network link 1078 typically provides information communication through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server 1092 connected to the Internet provides a service in response to information received over the Internet. For example, server 1092 provides information representing video data for presentation at display 1014.

The invention is related to the use of computer system 1000 for implementing the techniques described herein. According to one embodiment of the invention, those techniques are performed by computer system 1000 in response to processor 1002 executing one or more sequences of one or more instructions contained in memory 1004. Such instructions, also called software and program code, may be read into memory 1004 from another computer-readable medium such as storage device 1008. Execution of the sequences of instructions contained in memory 1004 causes processor 1002 to perform the method steps described herein. In alternative embodiments, hardware, such as application specific integrated circuit 1020, may be used in place of or in combination with software to implement the invention. Thus, embodiments of the invention are not limited to any specific combination of hardware and software.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server 1092 transmits program code for a particular application, requested by a message sent from computer 1000, through Internet 1090, ISP equipment 1084, local network 1080 and communications interface 1070. The received code may be executed by processor 1002 as it is received, or may be stored in storage device 1008 or other non-volatile storage for later execution, or both. In this manner, computer system 1000 may obtain application program code in the form of a signal on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red a carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

Figure 11:
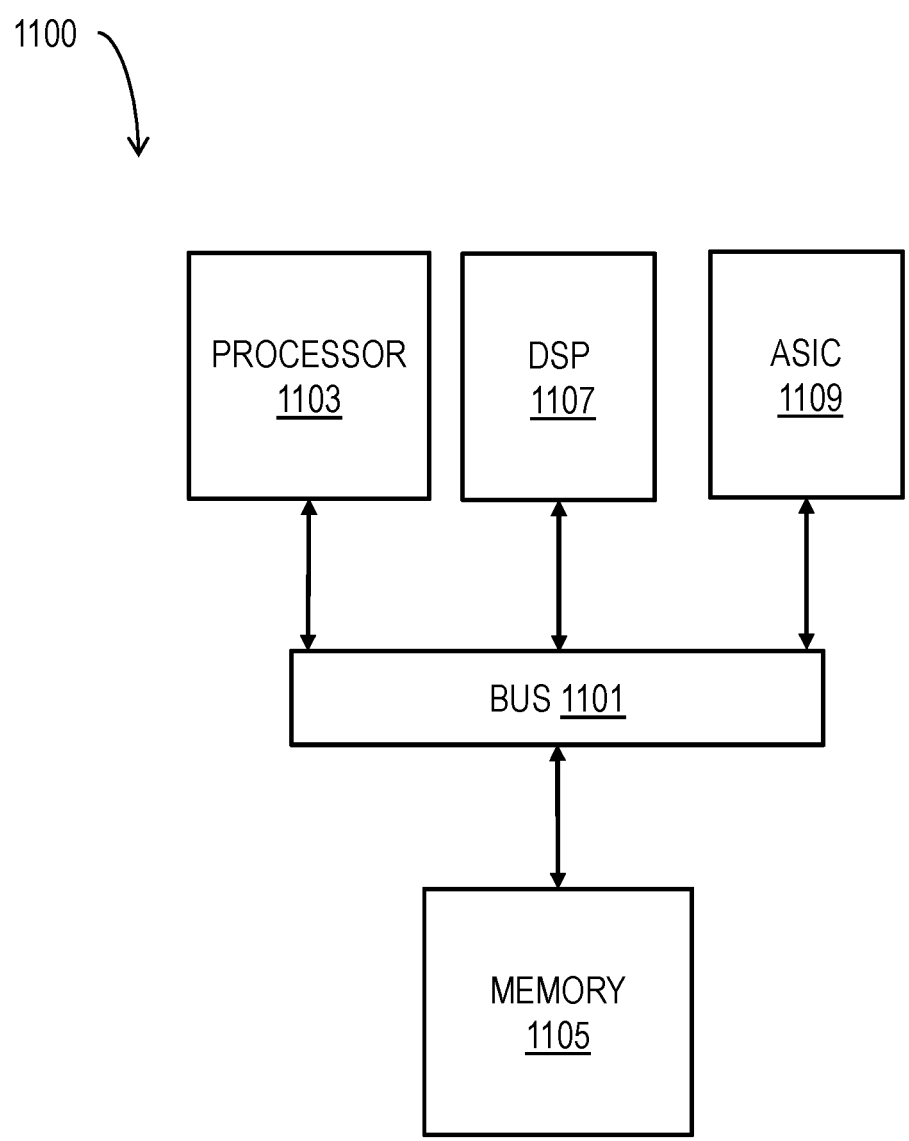
FIG. 11 illustrates a chip set upon which an embodiment of the invention may be implemented.

FIG. 11 illustrates a chip set 1100 upon which an embodiment of the invention may be implemented. Chip set 1100 is programmed to perform one or more steps of a method described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1100, or a portion thereof, constitutes a means for performing one or more steps of a method described herein.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1105 also stores the data associated with or generated by the execution of one or more steps of the methods described herein.

5. ALTERATIONS, EXTENSIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

6. REFERENCES

Agostinelli, S, Allison, J, Amako, K, Apostolakis, J, Araujo, H, Arce, P, Asai, M, Axen, D, Banerjee, S and Barrand, G 2003. Geant4-a simulation toolkit. Nuclear Instruments and Methods in Physics Research-Section A Only, 506, 250-303.

Andreyev, A, Sitek, A and Celler, A 2011. Fast image reconstruction for compton camera using stochastic origin ensemble approach. Medical physics, 38, 429.

Bennett, G, Archambeau, J, Archambeau, B, Meltzer, J and Wingate, C 1978. Visualization and transport of positron emission from proton activation in vivo. Science (New York, N Y), 200, 1151.

Brun, R and Rademakers, F 1997. Root—an object oriented data analysis framework. Nuclear Instruments and Methods in Physics Research Section A: Accelerators, Spectrometers, Detectors and Associated Equipment, 389, 81-86.

Deleplanque, M, Lee, I, Vetter, K, Schmid, G, Stephens, F, Clark, R, Diamond, R, Fallon, P and Macchiavelli, A 1999. Greta: Utilizing new concepts in [gamma]-ray detection*1. Nuclear Instruments and Methods in Physics Research Section A: Accelerators, Spectrometers, Detectors and Associated Equipment, 430, 292-310.

Enghardt, W and Müller, H 2005. In-beam pet at high-energy photon beams: A feasibility study. Phys. Med. Biol.

Hebert, T, Leahy, R and Singh, M 1990. Three-dimensional maximum-likelihood reconstruction for an electronically collimated single-photon-emission imaging system. JOSA A, 7, 1305-1313.

Icru 1993. Stopping power and ranges for protons and alpha particles Report 49. (Bethesda, Md.: International Commission on Radiation Units and Measurements)

Kang, B H and Kim, J W 2009. Monte carlo design study of a gamma detector system to locate distal dose falloff in proton therapy. Nuclear Science, IEEE Transactions on, 56, 46-50.

Kim, S M, Lee, J S, Lee, M N, Lee, J H, Lee, C S, Kim, C H, Lee, D S and Lee, S J 2007. Two approaches to implementing projector-backprojector pairs for 3d reconstruction from compton scattered data. Nuclear Instruments and Methods in Physics Research Section A: Accelerators, Spectrometers, Detectors and Associated Equipment, 571, 255-258.

Knopf, A, Parodi, K, Paganetti, H, Cascio, E, Bonab, A and Bortfeld, T 2008. Quantitative assessment of the physical potential of proton beam range verification with pet/ct. Physics in medicine and biology, 53, 4137.

Kroeger, R, Johnson, W, Kurfess, J, Phlips, B and Wulf, E 2002. Three-compton telescope: Theory, simulations, and performance. Nuclear Science, IEEE Transactions on, 49, 1887-1892.

Kurfess, J, Johnson, W, Kroeger, R and Phlips, B. Considerations for the next compton telescope mission. 2000. Citeseer, 789-793.

L'ecuyer, P 1996. Maximally equidistributed combined tausworthe generators. Mathematics of Computation, 65, 203-214.

Litzenberg, D, Bajema, J, Becchetti, F, Brown, J, Raymond, R, Roberts, D, Caraher, J, Hutchins, G, Ronningen, R and Smith, R. On-line monitoring and pet imaging of proton radiotherapy beams. 1992. IEEE, 954-956 vol. 2.

Mackin D, Peterson S, Beddar S and Polf J 2012 Evaluation of a stochastic reconstruction algorithm for use in Compton camera imaging and beam range verification from secondary gamma emission during proton therapy Phys. Med. Biol. 57 3537-53

Mackin D, Polf J, Peterson S and Beddar S 2013 The effects of Doppler broadening and detector resolution on the performance of three-stage Compton cameras Med. Phys. 40 012402.

McCleskey M, Kaye W, Mackin D, Beddar S, He Z and Polf J C 2015 Evaluation of a multistage CdZnTe Compton camera for prompt y imaging for proton therapy Nucl. Intstr. Met. Phys. Res. A 785 163-9.

Min, C H, Kim, C H, Youn, M Y and Kim, J W 2006. Prompt gamma measurements for locating the dose falloff region in the proton therapy. Applied physics letters, 89, 183517.

Moteabbed, M, Espana, S and Paganetti, H 2011. Monte carlo patient study on the comparison of prompt gamma and pet imaging for range verification in proton therapy. Physics in medicine and biology, 56, 1063-82.

Mundy, D W and Herman, M G 2010. Uncertainty analysis of a compton camera imaging system for radiation therapy dose reconstruction. Medical physics, 37, 2341.

Paans, A and Schippers, J 1993. Proton therapy in combination with pet as monitor: A feasibility study. Nuclear Science, IEEE Transactions on, 40, 1041-1044.

Parodi, K and Enghardt, W 2000. Potential application of pet in quality assurance of proton therapy. Physics in medicine and biology, 45, N151.

Parzen, E 1962. On estimation of a probability density function and mode. The Annals of Mathematical Statistics, 33, 1065-1076.

Peterson, S, Robertson, D and Polf, J 2010. Optimizing a three-stage compton camera for measuring prompt gamma rays emitted during proton radiotherapy. Physics in medicine and biology, 55, 6841.

Phillips, G W 1995. Gamma-ray imaging with compton cameras. Nuclear Instruments and Methods in Physics Research Section B: Beam Interactions with Materials and Atoms, 99, 674-677.

Polf, J, Peterson, S, Ciangaru, G, Gillin, M and Beddar, S 2009a. Prompt gamma-ray emission from biological tissues during proton irradiation: A preliminary study. Physics in medicine and biology, 54, 731.

Polf, J, Peterson, S, Mccleskey, M, Roeder, B, Spiridon, A, Beddar, S and Trache, L 2009b. Measurement and calculation of characteristic prompt gamma ray spectra emitted during proton irradiation. Physics in medicine and biology, 54, N519.

Robertson, D, Polf, J C, Peterson, S W, Gillin, M T and Beddar, S 2011. Material efficiency studies for a compton camera designed to measure characteristic prompt gamma rays emitted during proton beam radiotherapy. Physics in medicine and biology, 56, 3047.

Rosenblatt, M 1956. Remarks on some nonparametric estimates of a density function. The Annals of Mathematical Statistics, 832-837.

Schmid, G, Deleplanque, M, Lee, I, Stephens, F, Vetter, K, Clark, R, Diamond, R, Fallon, P, Macchiavelli, A and Macleod, R 1999. A [gamma]-ray tracking algorithm for the greta spectrometer. Nuclear Instruments and Methods in Physics Research Section A: Accelerators, Spectrometers, Detectors and Associated Equipment, 430, 69-83.

Scott, D W 1992. Multivariate density estimation, Wiley Online Library.

Siddon, R L 1985. Fast calculation of the exact radiological path for a three-dimensional ct array. Medical physics, 12, 252.

Sitek, A 2008. Representation of photon limited data in emission tomography using origin ensembles. Physics in medicine and biology, 53, 3201.

Solomon, C J and Ott, R J 1988. Gamma ray imaging with silicon detectors—a compton camera for radionuclide imaging in medicine. Nuclear Instruments and Methods in Physics Research Section A: Accelerators, Spectrometers, Detectors and Associated Equipment, 273, 787-792.

Testa, E, Bajard, M, Chevallier, M, Dauvergne, D, Le Foulher, F, Freud, N, Létang, J, Poizat, J C, Ray, C and Testa, M 2009. Dose profile monitoring with carbon ions by means of prompt-gamma measurements. Nuclear Instruments and Methods in Physics Research Section B: Beam Interactions with Materials and Atoms, 267, 993-996.

Wilderman, S J, Rogers, W, Knoll, G F and Engdahl, J C 1998. Fast algorithm for list mode back-projection of compton scatter camera data. Nuclear Science, IEEE Transactions on, 45, 957-962.

Zhang F and He Z 2006 New readout electronics for 3D position sensitive CdZnTe/HgI2 detector arrays IEEE Trans. Nucl. Sci. 53 3021-7

What is claimed is:

1. A method implemented on a processor comprising:
receiving first data indicating locations of a plurality of voxels of target resolution v in a target volume of a subject;
collecting from each of a plurality of detectors in one or more stages of a Compton camera within a coincidence time interval, location and deposited energy from an interaction associated with each high energy particle source event in the target volume, for a plurality of N source events in the target volume;
determining for each source event a cone of possible locations for the source event based on the locations and deposited energies collected from the plurality of detectors in one or more stages of the Compton camera;
initiating a stochastic origins ensemble (SOE) iterative algorithm by
  selecting for each source event a random location on the cone of possible locations for a corresponding source event and
  generating a histogram that indicates, for each voxel, a count of the selected locations that occur inside the voxel;
determining a solution comprising a set of N solution locations for the N source events from the SOE iterative algorithm after L iterations by
  updating for each source event during each iteration the selected location on the corresponding cone based at least in part on values of the counts in the histogram excluding the current source event, and
  updating the histogram based on the updated selected location for each source event during each iteration; and,
presenting, on a display device, data indicating at least one solution location of the set of N solution locations.

2. The method of claim 1, wherein each of the plurality of N source events is used once without replacement as the current source event, during each iteration of the L iterations.

3. The method of claim 1, wherein the source event is a gamma ray emission and the cause of the source event is a proton beam interacting with an atom in the subject.

4. The method of claim 1, wherein the source event is a gamma ray emission and the cause of the source event is a positron-emitting radionuclide as used in positron emission tomography (PET) medical imaging.

5. The method of claim 4, wherein collecting from each of the plurality of detectors in one or more stages of the Compton camera within the coincidence time interval, location and deposited energy from an interaction associated with the source event in the target volume further comprises selecting from each of only two detectors in one or more stages of the Compton camera within the coincidence time interval, location and deposited energy wherein a sum of the deposited energies in the two detectors is about equal to an energy of a gamma ray emitted by annihilation of the positron produced by the positron-emitting radionuclide.

6. The method of claim 1, wherein the source event is a gamma ray emission and the cause of the source event is a gamma-emitting radioisotope as used in single-photon emission computed tomography (SPECT) medical imaging.

7. The method of claim 6, wherein collecting from each of the plurality of detectors in one or more stages of the Compton camera within the coincidence time interval, location and deposited energy from an interaction associated with the source event in the target volume further comprises selecting from each of only two detectors in one or more stages of the Compton camera within the coincidence time interval, location and deposited energy wherein a sum of the deposited energies in the two detectors is about equal to an energy of a gamma ray emitted by the gamma-emitting radioisotope.

8. A computer-readable medium carrying one or more sequences of instructions, wherein execution of the one or more sequences of instructions by one or more processors causes the one or more processors to perform the steps of the method of claim 1.

9. A system comprising:
a Compton camera comprising a plurality of detectors in one or more stages, each stage comprising an array of detectors for a high energy particle;
at least one processor; and
at least one memory including one or more sequences of instructions,
the at least one memory and the one or more sequences of instructions configured to, with the at least one processor, cause the system to perform at least the steps of the method of claim 1.

10. A method implemented on a processor comprising:
a) receiving first data indicating locations of a plurality of voxels of target resolution v in a volume of a subject;
b) collecting from each of a plurality of detectors in one or more stages of a Compton camera within a coincidence time interval, location and deposited energy from an interaction associated with each high energy particle source event in the subject volume, for a plurality of N source events in the subject volume;
c) determining for each source event a cone of possible locations for the source event based on the locations and deposited energies collected from the plurality of detectors in one or more stages of the Compton camera,
d) initiating an instance of an stochastic origins ensemble (SOE) iterative algorithm by selecting for each source event a random location on the cone of possible locations for a corresponding source event;
e) determining an instance of a solution comprising a set of N solution locations for the N source events from the SOE iterative algorithm after L iterations;
f) repeating steps d and e for a plurality of M instances of the SOE iterative algorithm selecting for each source event M different random locations on the cone to initiate the plurality of M instances and to determine a plurality of M instances of a solution;
g) combining the plurality of M instances of the solution location for each source event to determine a combined solution location for each of the N source events; and
h) presenting, on a display device, data indicating the combined solution location for at least one source event of the N source events.

11. A computer-readable medium carrying one or more sequences of instructions, wherein execution of the one or more sequences of instructions by one or more processors causes the one or more processors to perform the steps of the method of claim 10.

12. A system comprising:
a Compton camera comprising a plurality of detectors in one or more stages, each stage comprising an array of detectors for a high energy particle;
at least one processor; and
at least one memory including one or more sequences of instructions,
the at least one memory and the one or more sequences of instructions configured to, with the at least one processor, cause the system to perform at least the steps of the method of claim 10.

* * * * *